(12) United States Patent
Takesako et al.

(10) Patent No.: US 7,491,511 B2
(45) Date of Patent: Feb. 17, 2009

(54) FUNGAL ANTIGENS AND PROCESS FOR PRODUCING THE SAME

(75) Inventors: Kazutoh Takesako, Otsu (JP);
Shigetoshi Mizutani, Shiga (JP);
Masahiro Endo, Kusatsu (JP);
Ikunoshin Kato, Uji (JP)

(73) Assignee: Takara Bio Inc., Otsu-shi (JP)

(*) Notice: Subject to any disclaimer, the term of this patent is extended or adjusted under 35 U.S.C. 154(b) by 231 days.

(21) Appl. No.: 11/280,416

(22) Filed: Nov. 17, 2005

(65) Prior Publication Data
US 2006/0068448 A1  Mar. 30, 2006

Related U.S. Application Data

(60) Division of application No. 09/987,190, filed on Nov. 13, 2001, now abandoned, which is a division of application No. 09/262,856, filed on Mar. 4, 1999, now Pat. No. 6,333,164, which is a continuation-in-part of application No. PCT/JP97/03041, filed on Aug. 29, 1997.

(30) Foreign Application Priority Data

Sep. 4, 1996 (JP) .................................. 8-255400
Mar. 31, 1997 (JP) .................................. 9-99775

(51) Int. Cl.
*C12P 21/06* (2006.01)
*C07H 21/04* (2006.01)
*C12N 1/00* (2006.01)

(52) U.S. Cl. ............... 435/69.1; 435/254.22; 435/254.1; 435/921; 536/23.1; 536/23.7

(58) Field of Classification Search ................ 435/69.1, 435/254.1, 254.22, 921; 536/23.1, 23.7
See application file for complete search history.

(56) References Cited

U.S. PATENT DOCUMENTS

| 5,275,814 | A | 1/1994 | Wojdani |
| 5,286,484 | A | 2/1994 | Rodriquez et al. |
| 6,432,407 | B1 | 8/2002 | Takesako et al. |
| 6,747,137 | B1 * | 6/2004 | Weinstock et al. ......... 536/23.1 |

FOREIGN PATENT DOCUMENTS

| GB | 1486330 | 9/1977 |
| JP | 6-169779 A | 6/1994 |

OTHER PUBLICATIONS

D. Navarro et al., Eur. J. Clin. Microbiol. Infect. Dis., vol. 12, No. 11 (1993), pp. 839-846.
R. A. Venezia et al., Am. J. Clin. Pathology, vol. 61, No. 6 (1974), pp. 849-855.
V.M. Hern et al., J. General Miclobiology, vol. 112 (1979), pp. 35-44.
A. Ishiguro et al., The American Society for Microbiology, vol. 60, No. 4 (Apr. 1992), pp. 1550-1557.
M. Moser et al., The Journal of Immunology, The American Society of Immunologists, vol. 149, No. 2, (Jul. 15, 1992), pp. 454-460.
S.J.N. Devi et al., The American Society for Microbiology, vol. 59, No. 10, (Oct. 1991), pp. 3700-3707.
Murray et al., Gene 61 (1987), pp. 401-413.
Bowie et al., Science, vol. 247 (1990), pp. 1306-1308.
Houghthten et al., Vaccines, Ed., Fred Brown (1986), Cold Spring Harbor Laboratory.
Okada et al., Eur. J. Biochem. 170 ( 1987), pp. 105-110.
Boehringer Mannheim Biochemicals Catalog (1991), p. 557.
Stralagene Product Catalog (1991), p. 66.
Gibco BRL Catalogue & Reference Guide (1992), p. 292.
Promega Catalog (1993/1994), pp. 90-91.
New England BioLabs Catalog (1986/1987), pp. 60-62.
Shen et al., Clinical and Experimental Allergy, vol. 19 (1989) pp. 191-196.
Buckley et al., Infect. Immun. vol. 37, No. 3 (Sep. 1982), pp. 1209-1217.
Rhei et al., Biochim. Biophys. Acta, vol. 1426, No. 3, Database GenEmbl. Acession No. AF031478 (1999), pp. 409-419.
Tsujita et al., J. Biochem, vol. 88, (1980) pp. 113-120.
Browing et al., Proc. Natl. Acad. Sci. USA, vol. 85 (Mar. 1988), pp. 1831-1834.
Else et al., FEBS, European Journal of Biochemistry, vol. 212 (1993), pp. 423-429.
Adra et al. PNAS, vol. 94 (1997), pp. 4279-4284.
Carla A. M. Marres, et al., "Nucleotide Sequence Analysis of the Nuclear Gene Coding for Manganese Superoxide Dismutase of Yeast Mitochondria, a Gene Previously Assumed to Code for the Rieske Iron-Sulphur Protein", European Journal of Biochemistry, vol. 147, 1985, pp. 153-161.
Suissa M. et al., "Isolation of the Nuclear Yeast Genes for Citrate Synthase and Fifteen Other Mitochondrial Proteins by a New Screening Method", Embo Journal, vol. 3, No. 8, 1984, pp. 1773-1781, XP002902395.
Rosario Cueva et al., "Yeast Vacuolar Aminopeptidase Yscl. Isolation and Regulation of the APE1 (LAP4) Structural Gene", FEBS Letters 1989, vol. 259, No. 1, pp. 125-129.
Hay, et al., "Delayed-Type Hypersensitivity Responses in Infected Mice Elicited by Cytoplasmic Fractions of *Cryptococcus neoformans*", Infection and Immunity, vol. 22, No. 1, pp. 72-79, Oct. 1978.
Crameri, R. et al., "Humoral and Cell-mediated Autoimmunity in Allergy to *Aspergillus fumigatus*", J. Exp. Med., (Jul. 1996), vol. 184, pp. 265-270.

* cited by examiner

*Primary Examiner*—Robert B Mondesi
*Assistant Examiner*—Padma V Baskar
(74) *Attorney, Agent, or Firm*—Birch, Stewart, Kolasch & Birch, LLP

(57) ABSTRACT

There can be provided a fungal antigen which is an insoluble fraction obtainable from fungal cells of which cell wall has been substantially removed or at least partially removed; a process for producing the same; a nucleic acid encoding the fungal antigen; a biologic product containing the fungal antigen; a method of stimulating immunological responses by using the biologic product; a method of suppressing allergic reaction to fungi in a vertebrate; and a method for diagnosing a disease caused by fungi in a vertebrate.

2 Claims, 9 Drawing Sheets

SEQUENCE LISTING

<160> NUMBER OF SEQ ID NOS: 15

<210> SEQ ID NO 1
<211> LENGTH: 50
<212> TYPE: PRT
<213> ORGANISM: Candida albicans
<220> FEATURE:
<221> NAME/KEY: Unsure
<222> LOCATION: (1)..(50)
<223> OTHER INFORMATION: any Xaa = any amino acid, unknown or other

<400> SEQUENCE: 1

Ala Ser Thr Lys Lys Tyr Asp Val Val Val Ile Gly Gly Gly Pro Gly
 1               5                  10                  15

```
Gly Tyr Val Ala Ala Ile Lys Ala Ala Gln Leu Gly Leu Asn Thr Ala
                20                  25                  30

Xaa Ile Glu Lys Arg Gly Ala Leu Gly Gly Thr Xaa Leu Asn Val Gly
        35                  40                  45

Xaa Ile
    50
```

<210> SEQ ID NO 2
<211> LENGTH: 30
<212> TYPE: PRT
<213> ORGANISM: Candida albicans
<220> FEATURE:
<221> NAME/KEY: Unsure
<222> LOCATION: (1)..(30)
<223> OTHER INFORMATION: any Xaa = any amino acid, unknown or other

<400> SEQUENCE: 2

```
Lys Tyr Ser Leu Pro Glu Leu Asp Tyr Glu Phe Ser Ala Thr Glu Pro
1               5                   10                  15

Tyr Ile Ser Gly Gln Ile Asn Glu Ile Xaa Tyr Thr Xaa Xaa
                20                  25                  30
```

<210> SEQ ID NO 3
<211> LENGTH: 31
<212> TYPE: PRT
<213> ORGANISM: Candida albicans

<400> SEQUENCE: 3

```
Ala Ser Ala Glu Pro Thr Leu Lys Gln Arg Leu Glu Glu Ile Leu Pro
1               5                   10                  15

Ala Lys Ala Glu Glu Val Lys Gln Phe Lys Lys Glu His Gly Lys
                20                  25                  30
```

<210> SEQ ID NO 4
<211> LENGTH: 30
<212> TYPE: PRT
<213> ORGANISM: Candida albicans

<400> SEQUENCE: 4

```
Lys Phe Thr Asp Asp Tyr Tyr Ser Lys Ile Ala Asp Tyr Ile Glu
1               5                   10                  15

Phe Thr Tyr Lys Asn Pro Thr Ile Tyr His Val Val Asn Phe
                20                  25                  30
```

<210> SEQ ID NO 5
<211> LENGTH: 491
<212> TYPE: PRT
<213> ORGANISM: Candida albicans

<400> SEQUENCE: 5

```
Met Leu Arg Ser Phe Lys Ser Ile Pro Ala Asn Gly Lys Leu Ala Gln
1               5                   10                  15

Phe Val Arg Tyr Ala Ser Thr Lys Lys Tyr Asp Val Val Ile Gly
                20                  25                  30

Gly Gly Pro Gly Gly Tyr Val Ala Ala Ile Lys Ala Ala Gln Leu Gly
            35                  40                  45

Leu Asn Thr Ala Cys Ile Glu Lys Arg Gly Ala Leu Gly Gly Thr Cys
    50                  55                  60

Leu Asn Val Gly Cys Ile Pro Ser Lys Ser Leu Leu Asn Asn Ser His
65                  70                  75                  80
```

```
Leu Leu His Gln Ile Gln His Glu Ala Lys Glu Arg Gly Ile Ser Ile
                85                  90                  95
Gln Gly Glu Val Gly Val Asp Phe Pro Lys Leu Met Ala Ala Lys Glu
            100                 105                 110
Lys Ala Val Lys Gln Leu Thr Gly Gly Ile Glu Met Leu Phe Lys Lys
        115                 120                 125
Asn Lys Val Asp Tyr Leu Lys Gly Ala Gly Ser Phe Val Asn Glu Lys
    130                 135                 140
Thr Val Lys Val Thr Pro Ile Asp Gly Ser Glu Ala Gln Glu Val Glu
145                 150                 155                 160
Ala Asp His Ile Ile Val Ala Thr Gly Ser Glu Pro Thr Pro Phe Pro
                165                 170                 175
Gly Ile Glu Ile Asp Glu Glu Arg Ile Val Thr Ser Thr Gly Ile Leu
            180                 185                 190
Ser Leu Lys Glu Val Pro Glu Arg Leu Ala Ile Ile Gly Gly Gly Ile
        195                 200                 205
Ile Gly Leu Glu Met Ala Ser Val Tyr Ala Arg Leu Gly Ser Lys Val
    210                 215                 220
Thr Val Ile Glu Phe Gln Asn Ala Ile Gly Ala Gly Met Asp Ala Glu
225                 230                 235                 240
Val Ala Lys Gln Ser Gln Lys Leu Leu Ala Lys Gln Gly Leu Asp Phe
                245                 250                 255
Lys Leu Gly Thr Lys Val Val Lys Gly Glu Arg Asp Gly Glu Val Val
            260                 265                 270
Lys Ile Glu Val Glu Asp Val Lys Ser Gly Lys Lys Ser Asp Leu Glu
        275                 280                 285
Ala Asp Val Leu Leu Val Ala Ile Gly Arg Arg Pro Phe Thr Glu Gly
    290                 295                 300
Leu Asn Phe Glu Ala Ile Gly Leu Glu Lys Asp Asn Lys Gly Arg Leu
305                 310                 315                 320
Ile Ile Asp Asp Gln Phe Lys Thr Lys His Asp His Ile Arg Val Ile
                325                 330                 335
Gly Asp Val Thr Phe Gly Pro Met Leu Ala His Lys Ala Glu Glu Glu
            340                 345                 350
Gly Ile Ala Ala Ala Glu Tyr Ile Lys Lys Gly His Gly His Val Asn
        355                 360                 365
Tyr Ala Asn Ile Pro Ser Val Met Tyr Thr His Pro Glu Val Ala Trp
    370                 375                 380
Val Gly Leu Asn Glu Glu Gln Leu Lys Glu Gln Gly Ile Lys Tyr Lys
385                 390                 395                 400
Val Gly Lys Phe Pro Phe Ile Ala Asn Ser Arg Ala Lys Thr Asn Met
                405                 410                 415
Asp Thr Asp Gly Phe Val Lys Phe Ile Ala Asp Ala Glu Thr Gln Arg
            420                 425                 430
Val Leu Gly Val His Ile Ile Gly Pro Asn Ala Gly Glu Met Ile Ala
        435                 440                 445
Glu Ala Gly Leu Ala Leu Glu Tyr Gly Ala Ser Thr Glu Asp Ile Ser
    450                 455                 460
Arg Thr Cys His Ala His Pro Thr Leu Ser Glu Ala Phe Lys Glu Ala
465                 470                 475                 480
Ala Leu Ala Thr Phe Asp Lys Pro Ile Asn Phe
                485                 490
```

<210> SEQ ID NO 6
<211> LENGTH: 188
<212> TYPE: PRT
<213> ORGANISM: Candida albicans

<400> SEQUENCE: 6

Ala Thr Glu Pro Tyr Ile Thr Gly Gln Met Asn Glu Ile His Tyr Thr
1               5                   10                  15

Lys His His Gln Thr Tyr Val Asn Asn Leu Asn Ala Ser Ile Glu Gln
            20                  25                  30

Ala Val Glu Ala Lys Ser Lys Gly Glu Val Lys Lys Leu Val Ala Leu
        35                  40                  45

Gln Lys Ala Ile Asn Phe Asn Gly Gly Tyr Leu Asn His Cys Leu
    50                  55                  60

Trp Trp Lys Asn Leu Ala Pro Val Ser His Gly Gly Gln Pro Pro
65                  70                  75                  80

Ser Glu Asp Ser Lys Leu Gly Lys Gln Ile Val Lys Gln Phe Gly Ser
                85                  90                  95

Leu Asp Lys Leu Ile Glu Ile Thr Asn Gly Lys Leu Ala Gly Ile Gln
            100                 105                 110

Gly Ser Gly Trp Ala Phe Ile Val Lys Asn Lys Ala Asn Gly Asp Thr
        115                 120                 125

Ile Asp Val Ile Thr Thr Ala Asn Gln Asp Thr Val Thr Asp Leu Asn
    130                 135                 140

Leu Val Pro Leu Ile Ala Ile Asp Ala Trp Lys His Ala Tyr Tyr Leu
145                 150                 155                 160

Gln Tyr Gln Asn Val Lys Ala Asp Tyr Phe Lys Asn Leu Trp His Val
                165                 170                 175

Ile Asn Trp Lys Glu Ala Glu Arg Arg Phe Glu Phe
            180                 185

<210> SEQ ID NO 7
<211> LENGTH: 1750
<212> TYPE: DNA
<213> ORGANISM: Candida albicans

<400> SEQUENCE: 7
ctcagagaga ccggactaaa gattctataa atattctttc tttctgttca cattatatat    60
tcttctcaac aaatgttaag atcattcaaa tctattccag ccaatggaaa attggcccag   120
tttgttagat atgcatcaac caagaaatac gacgttgttg tcattggtgg tggaccaggt   180
gggtacgttg ctgccatcaa ggccgctcaa ttaggattaa acactgcctg tattgaaaaa   240
agaggtgcat gggtggtac ttgtttgaat gttggttgta tcccatccaa atctttattg   300
aacaactccc atttattaca ccaaatccaa cacgaagcca agaaagagg tatttccatc   360 caaggtgaag ttggcgttga ttttccaaaa ttgatggctg ccaaggaaaa agccgtcaaa   420
caattgaccg gtggtattga atgttgttc aaaaagaaca aggttgacta cttgaaagga   480
gccggttctt tgttaacga aaaaaccgtc aaagtcactc caattgacgg cagcgaagca   540
caagaagttg aagccgacca catcatcgtt gctactgggt ctgaaccaac tccattccca   600
ggtattgaaa tagatgaaga aagaattgtc acttctactg gtattttatc attgaaagaa   660
gtaccagaaa gattagccat cattggtgga ggtatcattg gtttggaaat ggcttccgtt   720
tacgcaagat tgggctctaa agtcactgtt atcgaattcc agaacgctat tggtgccggt   780
atggatgctg aagttgctaa acaatctcaa aaattattgg ccaaacaagg tttggacttc   840

```
aaattaggta caaaggttgt taaaggtgaa agagatggtg aagtggtcaa gatcgaagtt      900
gaagatgtca aatccggtaa aaaatctgac cttgaagccg atgtcttgtt ggttgccatt      960
ggtagaagac catttactga aggttttgaac tttgaagcca ttggtttaga gaaagataac    1020
aagggaagat tgattattga cgaccaattc aagactaaac atgaccacat cagagttatt    1080
ggggatgtca cattcggtcc tatgttggcc cacaaggctg aagaagaagg tatcgctgct    1140
gctgaataca tcaagaaagg tcacggtcat gtaaactatg ctaacatccc ttctgttatg    1200
tatactcacc cagaagttgc ctgggttggt ttaaacgaag aacaattgaa agaacaaggc    1260
atcaaataca aagtaggtaa attcccattc attgccaact ccagagctaa aaccaacatg    1320
gacactgatg gtttcgtgaa attcattgct gatgccgaaa cccaaagagt gttgggtgtc    1380
cacattattg gtccaaatgc aggtgaaatg attgctgaag ctggtttggc cttagaatat    1440
ggtgcttcca ccgaagacat ttcaagaaca tgtcatgctc atccaacttt atctgaagct    1500
ttcaaggaag ctgctttggc caccttttgat aagccaatca acttttaaaa gtgatactga   1560
atacaacagt aatgaaaagt aaatactaaa ataatttgat ttgatttttt ttacttttttt   1620
ttcactcttt tgctctcatt tttaaggtta tctaaatact gaattatctg agccatataa    1680
gacaatcaca tctatacata aatacacaaa taataacaca tatatattta ttttgaaaaa    1740
aaaaaaaaaa                                                           1750

<210> SEQ ID NO 8
<211> LENGTH: 721
<212> TYPE: DNA
<213> ORGANISM: Candida albicans

<400> SEQUENCE: 8
gccactgaac cgtacatcac aggacaaatg aacgaaattc actacactaa acatcaccaa      60
acttatgtta caaaccttaa tgcttcaatt gaacaagccg ttgaagccaa atctaaaggt     120
gaagttaaaa aattggttgc cttacaaaaa gccatcaatt tcaacggtgg tggttacctc     180
aatcattgtt tgtggtggaa aaacttggct cctgtctctc acggtggtgg tcaaccacca     240
agtgaagatt ccaaattagg taaacaaatc gtcaaacaat ttggttcttt ggataaattg     300
attgaaatca ccaatggcaa attggctggt attcaaggtt ctggatgggc ttttattgtt     360
aaaaacaaag ccaatggtga tactattgat gtcatcacca ctgctaacca agatactgtt     420
actgatctaa acttggttcc attgattgct attgatgctt ggaaacatgc ttattatttg     480
caataccaaa atgttaaagc tgattacttc aagaaccttt ggcatgttat caactggaag     540
gaagctgaaa gaagatttga atttttaagtt actggacaaa agtcaagtac atatttaaat     600
ccaatattag aaaataaaag agttacttcc gatagtgctg attttgttta atatttcccc     660
attgtatata agtatatatg caagaatata ttcctgattg tgatgtaaaa aaaaaaaaaa     720
a                                                                     721

<210> SEQ ID NO 9
<211> LENGTH: 23
<212> TYPE: DNA
<213> ORGANISM: Artificial Sequence
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (9)
<223> OTHER INFORMATION: i
```

```
<220> FEATURE:
<221> NAME/KEY: modified_base
<222> LOCATION: (12)
<223> OTHER INFORMATION: i
<221> NAME/KEY: modified_base
<222> LOCATION: (15)
<223> OTHER INFORMATION: i
<220> FEATURE:
<223> OTHER INFORMATION: Description of Artificial Sequence: Synthetic
      DNA

<400> SEQUENCE: 9
ggntaygtng cngcnathaa rgc                                               23

<210> SEQ ID NO 10
<211> LENGTH: 23
<212> TYPE: DNA
<213> ORGANISM: Artificial Sequence
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (15)
<223> OTHER INFORMATION: i
<221> NAME/KEY: modified_base
<222> LOCATION: (18)
<223> OTHER INFORMATION: i
<220> FEATURE:
<223> OTHER INFORMATION: Description of Artificial Sequence: Synthetic
      DNA

<400> SEQUENCE: 10
tcytcngcyt trtgngcnar cat                                               23

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: Unsure
<222> LOCATION: (1)..(32)
<223> OTHER INFORMATION: any n = a,c,g,t unknown or other

<400> SEQUENCE: 11
aartaywsny tnccngaryt ngaytaygar tt                                     32

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: Unsure
<222> LOCATION: (1)..(32)
<223> OTHER INFORMATION: any n = a,c,g,t unknown or other

<400> SEQUENCE: 12
gcnacngarc cntayathws nggnca                                            26

<210> SEQ ID NO 13
<211> LENGTH: 944
<212> TYPE: DNA
<213> ORGANISM: Candida albicans
```

```
<400> SEQUENCE: 13
gggtacgtgg cggcgatcaa ggccgctcaa ttaggattaa acactgcctg tattgaaaaa        60
agaggtgcat tgggtggtac ttgtttgaat gttggttgta tcccatccaa atctttattg       120
aacaactccc atttattaca ccaaatccaa cacgaagcca agaaagagg catttctatc        180 caaggtgaag ttggcgttga ttttccaaaa ttgatggctg ccaaggaaaa agccgtcaaa       240
caattgaccg gtggtattga aatgttgttc aaaaagaaca aggttgacta cttgaaagga       300
gccggttctt ttgttaacga aaaaaccgtc aaagtcactc caattgacgg cagcgaagca       360
caagaagttg aagccgacca catcatcgtt gctactgggt ctgaaccaac tccattccca       420
ggtattgaaa tagatgaaga aagaattgtc acttctactg gtattttatc attgaaagaa       480
gtaccagaaa gattagccat cattggtgga agtatcattg gtttggaaat ggcttccgtt       540
tacgcaagat tgggctctaa agtcactgtt atcgaattcc agaacgctat tggtgccggt       600
atggatgctg aagttgctaa acaatctcaa aaattattgg ccaaacaagg tttggacttc       660
aaattaggta caaaggttgt taaaggtgaa agagatggtg aagtggtcaa gatcgaagtt       720
gaagatgtca aatccggtaa aaaatctgac cttgaagccg atgtcttgtt ggttgccatt       780
ggtagaagac catttactga aggtttgaac tttgaagcca ttggtttaga gaaagataac       840
aagggaagat tgattattga cgaccaattc aagactaaac atgaccacat cagagttatt       900
ggggatgtca cattcggtcc tatgctcgcc cacaaagccg aaga                       944

<210> SEQ ID NO 14
<211> LENGTH: 30
<212> TYPE: PRT
<213> ORGANISM: Candida albicans

<400> SEQUENCE: 14

Tyr Lys Val Ala Val Leu Gly Ala Gly Gly Ile Gly Gln Pro Leu
  1               5                  10                  15

Ser Leu Leu Leu Lys Leu Asn His Lys Val Thr Asp Leu Ala
             20                  25                  30

<210> SEQ ID NO 15
<211> LENGTH: 30
<212> TYPE: PRT
<213> ORGANISM: Candida albicans

<400> SEQUENCE: 15

Ala Pro Thr Phe Thr Asn Ser Asn Gly Gln Pro Ile Pro Glu Pro Phe
  1               5                  10                  15

Ala Thr Gln Arg Val Gly Gln His Gly Pro Leu Leu Leu Gln
             20                  25                  30
```

FUNGAL ANTIGENS AND PROCESS FOR PRODUCING THE SAME

This application is a divisional application of application Ser. No. 09/987,190, filed Nov. 13, 2001, now abandoned, which is a divisional application of application Ser. No. 09/262,856, filed on Mar. 4, 1999, which issued as U.S. Pat. No. 6,333,164 on Dec. 25, 2001, which is a continuation-in-part application of PCT/JP97/03041, filed Aug. 29, 1997; and this application claims priority of application Ser. No. 8-255400 filed in Japan on 09/04/1996 and application Ser. No. 9-99775 filed in Japan on 03/31/1997 under 35 U.S.C. § 119, the entire contents of which are herein incorporated by reference.

BACKGROUND OF THE INVENTION

1. Field of the Invention

The present invention relates to a fungal antigen effective for infectious diseases caused by fungi, which are pathogenic microorganisms, having cell wall, for prevention or treatment of allergoses, and for diagnosis of diseases caused by fungi, and a process for producing the same.

2. Discussion of the Related Art

It has been known that fungi infect vertebrates such as humans and animals to cause all kinds of diseases. For example, superficial mycosis is caused in human skin, oral, or the like; systemic mycosis is caused in internal organs, brain, or the like, and similar infectious diseases are also caused to animals such as pets and domestic animals. Among them, *Candida*, such as *Candida albicans*, *Cryptococcus*, such as *Cryptococcus neoformans*, *Aspergillus*, such as *Aspergillus fumigatus*, *Pneumocystis carinii*, or the like have been known as major causative fungi which cause systemic mycosis by infecting humans. *Candida* which infects skin, oral, vagina, or the like, and Dermatophytes such as *Trichophyton mentagrophytes* and *Trichophyton rubrum* which infects skin of hands, feet, or the like have been taken for major causative fungi for superficial mycosis.

A lot of Dermophytes are fungi which cause infectious diseases to domestic animals, and the like, and it has been known that *Microsporum* such as *Microsporum canis* and *Microsporum gypseum* are such fungi other than *Trichophyton*, such as *Trichophyton verrucosum* mentioned above. In addition to these fungi, a wide variety of fungi occur in the living environment, and are assumed to infect humans and animals. Furthermore, recently, by the frequent use of a wide range of antibiotics, use of immunosuppressants, use of immunosuppressive anticancer agents, etc., patients administered with these drugs have become immunocompromised hosts, and opportunistic infection with fungi of low pathogenicity have been increased in normal individuals administered therewith. Also, AIDS patients suffer from frequent onset of thrush and complications of various mycoses. Patients on treatment with intravascular catheter indwelling, especially intravenous hyperalimentation (IVH), are likely to develop infectious diseases caused by fungi, especially with *Candida* owing to catheter.

On the other hand, allergoses, typically including asthma, atopic dermatitis, and allergic rhinitis, have been increasing dramatically, among which a very large number of allergoses are caused by fungi.

As for a lot of allergoses, because of sensitization with a causative antigen of its disease, an IgE antibody (reagin antibody) specific to the antigen as an allergen is produced in serum and tissue, so that the IgE antibody is bound to mast cells and basophil receptors. When re-exposed to the same antigen, the IgE bound to the cells is crosslinked with the antigen on the cell surface, thereby resulting in physiological effects of IgE-antigen interaction. These physiological effects are exhibited via a release of chemical mediators, such as histamine, serotonin, heparin, eosinophilic chemotactic factor, and various leukotrienes. These effects can be systemic or topical, depending on the route of an antigen entering the body and the pattern of IgE sedimentation on the mast cells or basophils.

The systemic symptoms include anaphylactic shock, which causes intravascular IgE-basophil response to the antigen. As a consequence, smooth muscle contraction and capillary dilation take place as major changes, thereby resulting in symptoms such as eruption, vomiting, diarrhea, and dyspnea. In more severe cases, it may lead to death. In addition, the topical symptoms generally develop on the epithelium surface at the site of an antigen entering the body as shown by reddening and papules. When bronchiolar smooth muscle contraction develops as a topical symptom, it is manifested as bronchial asthma.

As the causative strains for causing allergoses, there have been known *Penicillium, Candida, Aspergillus, Alternaria, Cladosporium, Malassezia, Botrytis, Mucor, Rhizopus, Aureobasidium, Fusarium, Trichoderma, Helminthosporium, Neurospora, Wallemia, Rhodotorula,* and *Trichophyton*.

As the therapy for fungal infections, a treatment with an antifungal agent is generally employed. A large number of drugs for superficial mycoses have been developed, and some excellent drugs for systemic infections are available. In terms of efficacy, toxicity, adverse reactions, etc., however, their effects are unsatisfactory. For example, amphotericin B that has long been used, causes various adverse reactions, including serious renal dysfunction. Although various azole antifungal agents, typically including fluconazole, have been developed, infections are highly likely to recur because their action is static. Also, resistant strains are emerging due to frequent use. As the resistant strains emerge, the cross-resistance takes place, because many of the antifungal agents presently in practical use possess similar action mechanisms, which can pose a major problem. In cases of superficial mycoses, various therapeutic drugs have been developed, but none can be said to be satisfactory, because it requires a long-term treatment period and recurrence is repeated. Therefore, a development of a further improved drug has been in demand. Moreover, since a treatment with topical preparations only would be unsatisfactory for some superficial mycoses, e.g., nail tinea, these superficial mycoses would require systemic medication such as griseofulvin. In this case, long-term administration would be necessitated, which can cause various adverse reactions by the drugs. Also, as in superficial mycoses and AIDS-related thrush, since repetitive infection is caused, there is a major problem in terms of costs, even if an effective antifungal agent is developed. As described above, a treatment with an antifungal agent has various problems.

The living body naturally possesses an ability to protect against infection by fighting against such foreign-invading microorganisms. Vaccines utilize this ability. The prevention against infection with pathogenic bacteria has been carried out by vaccines and has been long used with fair efficacy. For such vaccines against bacterial infectious diseases, attenuated bacteria (*Mycobacterium tuberculosis*), killed bacteria (*Vibrio cholerae*), toxoids (*Corynebacterium diphtheriae, Clostridium tetani*), or purified antigens from capsular polysaccharides on cell surface (*Bordetella pertussis, Streptococcus pneumoniae*, influenza virus, *Neisseria meningitidis*) are employed as antigens. The vaccines provide an ability to protect against infection to the host by antibodies against antigenic molecules of the pathogen and by cellular immunity. It is considered that the antibodies serve to neutralize the toxic substances secreted by pathogens, and to prevent pathogens from invading host cells by binding to the cell surface molecules of the pathogen. In the cellular immunity, CD4+ cells and CD8+ T cells play a key role for recognizing the antigenic molecules of the pathogen and activating a protection reaction specific to the pathogen. Immunogenic substances, which are antigenic molecules possessed by the pathogens, have been isolated and identified, and some studies using these immunogens as sensitizing antigens (vaccines) have been made. In such cases, capsular polysaccharides, which are cell surface molecules as described above, are commonly used as immunogens.

An extremely large number and many kinds of fungi are present in the environment, and almost all vertebrates are sensitized with these fungi. Also, a large number of fungi are commonly present in the living bodies. The vertebrates are, therefore, generally provided with various immunological reactions for body protection against these fungi. Immunological reactions which have important roles against fungal infections show the phagocytosis and fungicidal actions of activated macrophages and polymorphonuclear leukocytes (PMN) and play a main role, and are also known to contribute to antibodies and cellular immunity. On their cell surface, fungi have a cell wall, comprising, as a main component, polysaccharides, such as mannan, glucan, and chitin, of which the content accounts for nearly 30% of the entire cell in some fungal cells [Klis, R. U. et al., *Yeast*, Vol. 10, 851-869, (1994)]. Of these cell wall components, mannan is the most antigenic. The mannan is a polysaccharide in the cell surface layer, and an antibody against the polysaccharide moiety is produced in large amounts. The cell wall glucans from fungi, typically including Zymosan, possess various biological activities, and are known to possess non-specific immunopotentiating actions. It is assumed that the cell wall components, including mannan on a cell surface of fungi, play an important role in causing infection as an adhesion molecule to the living body of cells.

Also, *Cryptococcus galactoxylomannan* [Devi, S. J. N. et al., *Infect. Immun.*, Vol. 59, 3700-3707 (1991)] and the *Candida albicans* adhesion factor phosphomannoprotein (WO 95/31998) have been reported to serve as vaccines, and antibodies against these antigenic molecules have been reported to possess protection activity against infection. Regarding the induction of immunological protection against infection with living or dead *Candida* cells, a large number of reports have been made [Segal, E. et al., *Critical Reviews in Microbiology*, Vol. 14, 229-271 (1987)]. In this case as well, it has been assumed that an immunological reaction mainly functions for body protection against the cell wall components which are the cell surface molecules.

Other vaccines against fungi include the ribosome vaccine [Segal, E., *Handbook of Applied Mycology, Volume 2: Immunizations against fungal diseases in man and animals., Humans, animals and insects*] has been tested for infectious diseases caused by fungi, typically including *Candida albicans* and *Trichophyton*, and studied on laboratory animals and partially on humans and domestic animals. Recently, there have been reported that enolase and stress protein HSP90 (Japanese Unexamined Patent Publication No. Hei 4-502257) can induce protective activity against infection.

However, it cannot be said that all of the above-mentioned antigenic molecules are confirmed to have satisfactory efficacy. Also, it is doubtful whether or not satisfactory efficacy can be obtained in highly diversified mammals by treatment with a single antigenic molecule.

On the other hand, therapies for allergoses include the use of antihistaminic drugs, steroidal anti-inflammatory drugs, chemical mediator release suppressors, and the like. It should be noted, however, that the antihistamines have a risk of developing various adverse reactions, such as malaise, drowsiness, and vertigo, that the steroids have a risk of developing various adverse reactions, such as adrenal atrophy and dysfunction, and gastric ulcer, and that the chemical mediator release suppressors have a risk of also suppressing the action of chemical mediators involved in conditions other than the allergosis of interest. From this viewpoint, prevention method for reducing the chance of exposure to allergens specified by antigen diagnosis, and/or desensitization therapy using such causative allergens is considered to be an excellent therapy.

In allergoses, it is therefore necessary to first diagnose for identifying the causative antigen, and for this purpose, more than 100 kinds of commercially available allergen extracts, sometimes those prepared by the laboratory, are subjected to intradermal test for suspected antigen extracts. After a highly likely antigen is found, the antigen can be specified by determination of IgE antibody titer in sera, challenge test, or histamine release test using whole blood or lymphocytes.

As allergens by which allergic symptoms are provoked in humans, a large number of naturally occurring ones have been known. Commercially available food and other allergen extracts are supplied as crude extracts from natural allergens. Therefore, they are naturally agglomerates of many substances and contain a plurality of antigens. Recently, as a result of advances in separation and purification techniques and evaluation methods for allergen activity, antigenic proteins, which comprise the main body of allergens, are isolated and identified from a variety of food allergens.

Also, from each of allergens occurring in the environment, such as mites, *Cryptomeria japonica* pollen, and feline hair, antigenic proteins named as Der p I [Smith, W. A. et al., *Clin. Exp. Allergy*, Vol. 24, 220-228 (1994)], Cry j I [Sone, T. et al., *Biochem. Biophys. Res. Commun.*, Vol. 199, 619-625 (1994)], and Fel d I [Morgenstern, J. P. et al., *Proc. Natl. Acad. Sci. USA*, Vol. 88, 9690-9694 (1991)] have been isolated as major allergens. Furthermore, the genes encoding these allergen proteins have been isolated, so that pure allergen proteins can be prepared in large amounts by genetic engineering techniques.

In the meantime, efforts have been made to isolate allergens derived from fungi. Antigenic proteins have been isolated and identified from proteins existing in fungal cells. For example, alcohol dehydrogenase (Can a I) [Shen, H. D. et al., *Clin. Exp. Allergy*, Vol. 21, 675-681 (1991)] and enolase [Ishiguro, A. et al., *Infect. Immun.*, Vol. 60, 1550-1557 (1992)] have been isolated from *Candida albicans* and identified, and ribotoxin (Asp f Ia) [Mosor, M. et al., *J. Immunol.*, Vol. 149, 454-460 (1992)] have been isolated from *Aspergillus fumigatus* and identified, some of which have been known to act as allergens.

Generally, in the case of allergens from fungi, including *Candida* and *Aspergillus*, however, there are few cases where a single major allergen exists as an antigenic protein, but a plurality of antigenic proteins exist [Stewart, G. A. et al., *Clin. Exp. Allergy*, Vol. 26, 1020-1044 (1996)], in which different antigens by depending upon individuals, or a plurality of antigens for each individual, are recognized as allergens, to which the individuals react. In other words, even when the individuals are allergic to *Candida*, for instance, it is known that in many cases antigens to which each individual reacts are different antigens, and that each individual reacts to a plurality of antigens derived from *Candida*.

Presently commercially available diagnostic or therapeutic allergen extracts are for the most part simple extracts or hardly purified crude extracts, so that the included ingredients are substantially uncontrolled. The allergen extracts from fungi include those from *Candida, Aspergillus, Alternaria, Cladosporium, Malassezia, Penicillium*, and the like. However, the methods for production thereof differ from those for the allergen extracts from naturally occurring allergens in food or the environment described above. In other words, these extracts are not supplied as cultured cells of the causative fungus per se, but prepared from an extracellular product secreted in the culture broth as raw material, which can be considered as a side-product, obtained by subjecting a representative strain belonging to each genus to a long-term cultivation in a chemically defined medium containing a limited nutrient source. Therefore, the antigen obtainable by such production method is an autolysate of cells or an extracellular secretion, which presumably comprises, as a main component, cell wall polysaccharides typically including mannan and glucan. However, neither the contents of these antigens nor the kinds of other antigenic proteins have yet been clarified. In addition, sufficient care should be paid for its use, since their quality is diversified among manufacturers.

Cell wall polysaccharides richly contained in commercially available allergen extracts from fungi, especially mannan, serve as major allergens in some patients with allergy on one hand, and even normal individuals have large amounts of IgG and IgM against cell wall polysaccharides. In addition, mannan per se, especially neutral mannan, has been known to possess toxicity, including lethal action to the mouse [*Japanese Journal of Medical Mycology*, Vol. 36, 203-208 (1995)]. It has been also known that cell wall glucan possesses pathological actions, including induction of inflammation [Kogan, G. et al., *Biomedical and Biotechnological Advances in Industrial Polysaccharides*, 251-258 (1989)].

The use of mannan and other cell wall components, which are antigens, or fungal cells per se, as vaccines, therefore, involves risks, such as causation of hypersensitivity. Also, in desensitization therapy etc. for allergoses, cell wall components do not always act as major allergens; therefore, when an allergen composition containing a cell wall component is used, its antigenicity is of concern, necessitating to be cautious when administering to humans. In this respect, presently available allergen extracts from fungi are completely unsatisfactory. Moreover, there are no known diagnostic and/or therapeutic pharmaceutical compositions in which a sufficient amount of an effective antigen is contained.

As described above, a development of novel therapeutic drugs of high efficacy and higher safety for mycoses is strongly desired, from the viewpoints of increasing incidence of mycoses, and further problems related to adverse reactions, development of resistant strains, medical costs, etc. in antifungal agents presently in use. The vaccines are advantageous over antifungal agents in many aspects, and if vaccines for such infectious diseases caused by fungi could be found, it would not only make it possible to prevent pain and weakening owing to being taken these infectious diseases, but also enable definite reduction of the dosage of drugs intended for the treatment of these infectious diseases. Furthermore, by avoiding the use of the drugs in such a way, selective pressure on pathogenic microorganisms due to overdoses of the antifungal agents is reduced, so that the prevalence of the resistant strains can be reduced. At present, however, no such highly effective vaccines have yet been found. Also, it is expected that sensitizing with a plurality of antigens has better induction of prevention against infection than sensitizing with a single antigen in the aspects of resistance and efficacy.

On the other hand, with the increase in the incidence of allergoses, numerous therapeutic or diagnostic allergen extracts have become commercially available, many of which effective ingredients, however, have not yet been clarified. As for fungi, although it remains unknown from which portions of the fungal cells the components are derived, from the methods for their production, it is assumed that its major component is polysaccharides derived from cell wall, clearly having a low content of antigenic components derived from intracellular components, and thus having a very uneven distribution in the antigenic component. For this reason, it is considered that satisfactory treatment or diagnosis cannot be carried out by using commercially available allergen extracts from fungi, and antigen extracts obtained by similar methods. Therefore, it is expected that allergen extracts having ingredients differing from those contained in conventional allergen extracts, and that the amounts of ingredients of those allergen extracts differing from those of conventional allergens exhibit high efficacy. Also, as for the present therapy of desensitization, which is considered effective for allergoses, it is necessary that an antigenic liquid is administered intradermally in small dosages at a time, once or twice a week, with increased dosage to a level maintained over a 3- to 4-month period, the administration of which is continued for 1 to 3 additional years. By the use of an antigen composition capable of easy volume increase and/or increased dosage, therefore, it is expected that an excellent therapeutic effect can be more easily obtained. Also, mammals typically including humans are generally diverse, and it is very likely that those recognized as antigens are different even if infected with, or becomes allergic to, one kind of fungus. Antigens containing sufficient amounts of diversified antigenic components are, therefore, desirable.

Furthermore, it is diagnostically important to specify the causative antigen when choosing an effective therapy, whereby highly effective and safer treatments, such as desensitization therapy using the antigen, can be carried out. It is, therefore, preferable from these viewpoints to specify unknown antigens.

Accordingly, an object of the present invention is to provide a fungal antigen that can be used for effective, safer biologic products against diseases caused by such fungi, including, for instance, vaccine compositions, compositions for desensitization therapy, and diagnostic compositions. A further object of the present invention is to provide a method for producing the fungal antigen, and a nucleic acid encoding the fungal antigen.

These and other objects of the present invention will be apparent from the following description.

SUMMARY OF THE INVENTION

Since some of the cell wall components from fungi, which have conventionally been studied mainly as antigenic molecules, cause immunological reactions undesirable to living bodies, the present inventors have studied for substances that possess antigenicity, and activity as vaccines and/or allergens for components other than cell wall components, using protoplasts, as starting materials, obtained by removing the cell wall from fungal cells. As a result, the present inventors have clarified that insoluble fractions containing cytoplasmic membrane proteins and membrane proteins of cell organelle, obtained from protoplasts derived from fungi causative for infectious diseases, unexpectedly possess potent antigenicity. They have further clarified that even though the insoluble fractions substantially do not contain cell wall components, their activity as vaccines is at an equivalent level or higher than that of living cells. The present inventors have also clarified that a solubilized fraction obtainable from the insoluble fraction using a solubilizer, such as a surfactant, also possesses potent antigenicity and potent activity as vaccines.

Furthermore, the present inventors have clarified that since the product of the present invention can be obtained as a mixture of several kinds of antigens, it is expected to provide a broader range of immunological responses than a case of administration of a particular single antigenic component, and that in fact possesses more potent vaccine activity than any of antigenic components that have been conventionally studied. The present inventors have further clarified that the antigen acts to stimulate immunocytes, typically including lymphocytes, to possess an activity for releasing cytokines, such as IFN-γ from the cells. The cytokine-releasing cells include, for example, T lymphocytes, natural killer (NK) cells, and the like. On the other hand, the present inventors have clarified that the insoluble fraction obtainable from protoplasts derived from causative fungi of allergoses possesses potent antigenicity and sufficient activity as allergens. The present inventors have also clarified that the solubilized fraction obtainable from the insoluble fractions by using a solubilizer, such as a surfactant, also possesses potent antigenicity and sufficient activity as allergens. In addition, the present inventors have clarified that the insoluble fraction obtainable from protoplasts derived from causative fungi of diseases and/or the solubilized fraction obtainable from the insoluble fraction possesses sufficient activity for diagnostic antigens. Further, the present inventors have succeeded in isolating a protein possessing antigenicity that has not conventionally been elucidated from the fractions. The present invention has been completed.

Specifically, the present invention is summarized as follows:

[1] a fungal antigen characterized in that the fungal antigen is an insoluble fraction obtainable from fungal cells of which cell wall has been substantially removed or at least partially removed;

[2] a fungal antigen comprising an antigenic protein having a vaccine activity or an allergen activity originated from *Candida albicans*, wherein the antigenic protein comprises the partial amino acid sequence as shown by SEQ ID NO: 1 in Sequence Listing and has a molecular weight of about 65,000 as determined by SDS-PAGE under reduced conditions;

[3] a fungal antigen comprising a peptide comprising an entire sequence of the amino acid sequence as shown by SEQ ID NO: 5 in Sequence Listing, or a partial sequence thereof, the peptide having a vaccine activity or an allergen activity;

[4] a fungal antigen comprising an antigenic protein having a vaccine activity or an allergen activity originated from *Candida albicans*, wherein the antigenic protein comprises the partial amino acid sequence as shown by SEQ ID NO: 2 in Sequence Listing and has a molecular weight of about 25,000 as determined by SDS-PAGE under reduced conditions;

[5] a fungal antigen comprising a peptide comprising an entire sequence of the amino acid sequence as shown by SEQ ID NO: 6 in Sequence Listing, or a partial sequence thereof, the peptide having a vaccine activity or an allergen activity;

[6] a fungal antigen comprising an antigenic protein having a vaccine activity or an allergen activity originated from *Candida albicans*, wherein the antigenic protein comprises the partial amino acid sequence as shown by SEQ ID NO: 3 in Sequence Listing and has a molecular weight of about 30,000 as determined by SDS-PAGE under reduced conditions;

[7] a fungal antigen comprising an antigenic protein having a vaccine activity or an allergen activity originated from *Candida albicans*, wherein the antigenic protein comprises the partial amino acid sequence as shown by SEQ ID NO: 4 in Sequence Listing and has a molecular weight of about 62,000 as determined by SDS-PAGE under reduced conditions;

[8] a fungal antigen comprising an antigenic protein having a vaccine activity or an allergen activity originated from *Candida albicans*, wherein the antigenic protein comprises the partial amino acid sequence as shown by SEQ ID NO: 14 in Sequence Listing and has a molecular weight of about 35,000 as determined by SDS-PAGE under reduced conditions;

[9] a fungal antigen comprising an antigenic protein having a vaccine activity or an allergen activity originated from *Candida albicans*, wherein the antigenic protein comprises the partial amino acid sequence as shown by SEQ ID NO: 15 in Sequence Listing and has a molecular weight of about 55,000 as determined by SDS-PAGE under reduced conditions;

[10] a process for producing a fungal antigen which is an insoluble fraction obtainable from fungal cells of which cell wall has been substantially removed or at least partially removed, characterized in that the process comprises the steps of:
(1) obtaining living fungal cells;
(2) obtaining fungal cells of which cell wall has been substantially removed or at least partially removed;
(3) bursting the fungal cells of which cell wall has been substantially removed or at least partially removed; and
(4) obtaining an insoluble fraction;

[11] a process for producing a fungal antigen which is a solubilized fraction extracted and separated from an insoluble fraction obtainable from fungal cells of which cell wall has been substantially removed or at least partially removed, characterized in that the process comprises the steps of:
(1) obtaining living fungal cells;
(2) obtaining fungal cells of which cell wall has been substantially removed or at least partially removed;
(3) bursting the fungal cells of which cell wall has been substantially removed or at least partially removed;
(4) obtaining an insoluble fraction; and
(5) extracting and separating a solubilized fraction from the insoluble fraction;

[12] a biologic product containing the fungal antigen of item [1] above, or a fungal antigen produced by the process of item [10] or [11] above;

[13] a cytokine releasing agent containing the fungal antigen of item [1] above, or a fungal antigen produced by the process of item [10] or [11] above;

[14] an allergen composition for preventing allergoses against fungi or exhibiting therapeutic effects therefor by administering to individuals, characterized in that the allergen composition contains the fungal antigen of item [1] above, or a fungal antigen produced by the process of item [10] or [11] above; and

[15] a diagnostic composition for a disease caused by fungi, characterized in that the diagnostic composition contains the fungal antigen of item [1] above, or a fungal antigen produced by the process of item [10] or [11] above.

DETAILED DESCRIPTION OF THE INVENTION

Figure 1A:
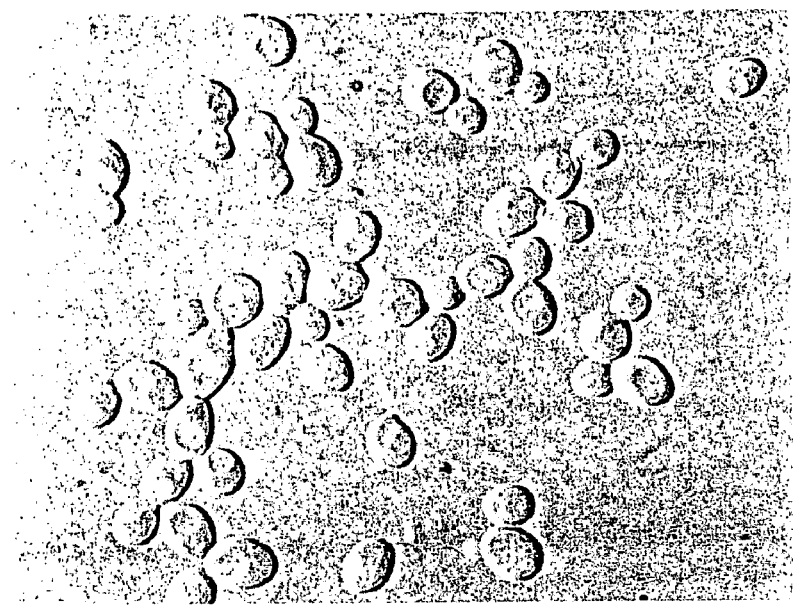
FIG. 1 is figures showing morphologies before and after cell wall removal from *Candida albicans* TIMM 1768 cells (yeast type), the figures being taken at a magnification of ×1,000 using a differential interference microscope (manufactured by NIKON Corporation), wherein A shows cells before cell wall removal, and B shows cells after cell wall removal.

The present invention is hereinafter described in detail.

The fungal antigen of the present invention is characterized in that the fungal antigen is an insoluble fraction obtainable from fungal cells of which cell wall has been substantially removed or at least partially removed. Such fungal antigens can be, for example, used as biologic products. The fungal antigen of the present invention is obtained from a causative fungus of an infectious disease or a causative fungus of an allergosis. The fungal antigen derived from a causative fungus of an infectious disease is capable of inducing immunity against infection in vertebrates, so that the fungal antigen can be suitably used particularly as a composition of vaccine. On the other hand, the fungal antigen derived from a causative fungus of an allergosis can be utilized to desensitize vertebrates, so that the fungal antigen can be suitably used to prevent and treat allergoses. Furthermore, such fungal antigens can suitably be used to diagnose diseases caused by fungi.

1. Fungal Cells

The fungi usable in the present invention are not particularly limited, and they include not only fungi possessing pathogenicity in vertebrates such as humans and animals, but also other fungi closely related thereto. Examples thereof include one or more fungi selected from the group consisting of fungi belonging to *Candida*, *Aspergillus*, *Cryptococcus*, *Mucor*, *Rhizopus*, *Absidia*, *Nocardia*, *Histoplasma*, *Blastomyces*, *Coccidioides*, *Trichophyton*, *Microsporum*, *Epidermophyton*, *Sporothrix*, Dematiaceous fungi, *Malassezia*, *Pneumocystis*, *Penicillium*, *Alternaria*, *Cladosporium*, *Botrytis*, *Aureobasidium*, *Fusarium*, *Trichoderma*, *Helminthosporium*, *Neurospora*, *Wallemia*, and *Rhodotorula*.

In the present invention, fungal infectious diseases in vertebrates include candidiasis, aspergillosis, cryptococcosis, mucormycosis, actinomycosis, histoplasmosis, blastomycosis, various skin mycoses, tinea versicolor, and *Pneumocystis carinii* pneumonia in humans. It is, therefore, preferable from the viewpoint of usefulness that the fungus usable in a vaccine composition in the present invention is a causative fungus of such a fungal infectious disease.

Concrete examples thereof include causative fungi of candidiasis such as *Candida albicans*, *C. tropicalis*, and *Candida glabrata*; causative fungi of aspergillosis such as *Aspergillus fumigatus* and *Aspergillus flavus*; causative fungi of cryptococcosis such as *Cryptococcus neoformans*; causative fungi of mucormycosis such as *Mucor* sp., *Absidia* sp., and *Rhizopus* sp.; causative fungi of actinomycosis such as *Nocardia asteroides*; causative fungi of other fungal infectious diseases in the internal organs such as *Trichosporon cutaneum*, *Rhodotorula glutinis*, *Geotrichum candidum*, *Pneumocystis carinii*, *Coccidioldes immitis*, *Paracoccidioides brasiliensis*, *Histoplasma capsulatum*, and *Blastomyces dermatitidis*; *Tricophyton*, which is Dermatophytes, such as *Tricophyton mentagrophytes*, *Tricophyton rubrum*, and *Tricophyton verrucosum*; *Microsporum* such as *Microsporum canis*, *Microsporum gypseum*, and *Epidermophyton* sp.; *Phialophora* sp. and *Cladosporium* sp., which are Dematiaceous fungi; *Malassezia furfur*, which causes tinea versicolor; causative fungi for other skin mycoses such as *Sporothrix schenckii* and *Fonsecaea pedrosoi*, and the like.

The usable fungal strain is not particularly limited, as long as it is closely related to the causative fungus of the mycosis to be treated or prevented, and a strain possessing pathogenicity (e.g., lethal toxicity against mice) is desirable. Typical examples of the useful strains include *Candida albicans* ATCC 10231, TIMM 1768, and TIMM 0239 for candidiasis; *Aspergillus fumigatus* ATCC 28212, ATCC 42202, and TIMM 1776 for aspergillosis; and *Cryptococcus neoformans* ATCC 24067, TIMM 0354, and capsule-deficient *Cryptococcus neoformans* TIMM 0357 for cryptococcosis. In addition, *Candida utilis*, yeasts of *Saccharomyces* such as *Saccharomyces cerevisiae*, yeasts of *Kluyveromyces* such as *Kluyveromyces marxianus* and *Kluyveromyces lactis* have been known to be closely related to *Candida albicans*, which are also usable in the present invention.

When used for the purpose of releasing a cytokine from cells, the fungal antigen is preferably derived from a normally colonizing fungus to which even normal individuals are immunologically sensitized, with a preference given to an antigen derived from *Candida albicans*.

On the other hand, when used to suppress an allergic reaction, the fungus usable for preparing the fungal antigen contained in the allergen composition of the present invention is preferably a causative fungus that provokes allergic symptoms in humans, from the viewpoint of its usefulness.

Concrete examples thereof include *Candida* such as *Candida albicans*, *Candida tropicalis*, *Candida glabrata*, and *Candida boidinii*; *Aspergillus* such as *Aspergillus fumigatus*, *Aspergillus restrictus*, and *Aspergillus* versicolor; *Trichophyton* such as *Trichophyton mentagrophytes*; *Malassezia* such as *Malassezia furfur*; *Mucor* such as *Mucor racemosus*; *Rhizopus* such as *Rhizopus oryzae*; *Penicillium* such as *Penicillium notatum*; *Alternaria* such as *Alternaria alternata* and *Alternaria kikuchiana*; *Cladosporium* such as *Cladosporium cladosporioides*, and *Cladosporium carionii*; *Botrytis* such as *Botrytis cinerea*; *Aureobasidium* such as *Aureobasidium pullulans*; *Fusarium* such as *Fusarium oxysporum*; *Trichoderma* such as *Trichoderma viridae*; *Helminthosporium* such as *Helminthosporium maydis*; *Neurospora* such as *Neurospora crassa*; *Wallemia* such as *Wallemia sebi*; *Rhodotorula* such as *Rhodotorula glutinis*, and the like.

The usable fungal strain is not particularly limited, as long as it is closely related to the causative fungus of the allergosis to be treated or prevented. Typical examples thereof include *Candida* such as *Candida albicans* ATCC 10231 and TIMM 1768, and *Candida boidinii* ATCC 18810 for preparing *Candida* antigens; *Aspergillus* such as *Aspergillus fumigatus* ATCC 28212 and TIMM 1776, and *Aspergillus restrictus* ATCC 16912 for preparing *Aspergillus* antigens; *Alternaria* such as *Alternaria alternata* IFO 31188 for preparing *Alternaria* antigens; *Malassezia* such as *Malassezia furfur* ATCC 14521 and TIMM 2782 for preparing *Malassezia* antigens; and the like.

In the present invention, in the case of a fungal antigen usable for diagnosing a disease caused by a fungus, the usable fungus is preferably the above-described fungi that causes the disease.

2. Fungal Antigens

The "fungal cells of which cell wall has been substantially removed" in the phrase "fungal cells of which cell wall has been substantially removed or at least partially removed," as used in the present specification, refer to the protoplasts or protoplast-like cells of the fungal cells. The "fungal cells of which cell wall has been at least partially removed" refer to the spheroplasts or spheroplast-like cells of the fungal cells. Specifically, typical fungal cells of which cell wall has been substantially removed are the protoplasts of the fungal cells, and typical fungal cells of which cell wall has been at least partially removed are the spheroplasts of the fungal cells. Accordingly, the phrase "insoluble fraction obtainable from fungal cells of which cell wall has been substantially removed or at least partially removed" means that the insoluble fraction is obtainable from the protoplasts, spheroplasts, or the like, of the fungal cells.

The phrase "the cell wall has been at least partially removed" means that cell wall-constituents, for example, mannan or glucan, are removed to an extent that the function of the cell wall such as morphological maintenance or osmotic pressure resistance to hypotonic solutions is lost, and that at the same time the cell wall is removed to an extent so as to at least not to cause any adverse effects of the cell wall component. In the present invention, it is preferable to use the fungal cells of which cell wall has been substantially removed. However, the fungal cells used may have cell wall components partially remaining therein, as long as the components derived from the cell wall do not give any adverse effects, such as hypersensitivity or lethality, on the living body, when administered to the living body. Specifically, the insoluble fraction contains relatively large intracellular structures, such as cell membranes, cell organelle (mitochondria, nuclei, lysosome, vacuoles, etc.), and cell organelle membranes; a protein bound to the cell membrane; and a protein bound to the cell organelle membrane. The insoluble fraction in the present invention needs not contain all the above-mentioned components, as long as it contains at least one of the components.

This insoluble fraction may further contain phospholipids, glycolipids, and other lipids, sugars, nucleic acids, etc. Moreover, in a case where the fungal cells of which cell wall partially remains therein are used, when the fungal antigen of the present invention is administered to the living body, it may contain components derived from the cell wall, as long as the components do not give any adverse effects, such as hypersensitivity or lethality, quantitatively or qualitatively on the living body. The amount of contamination with these antigenic components derived from the cell wall can, for example, be quantified by determining the inhibitory activity against an agglutination reaction using an antiserum against the cell wall component as described in Examples below.

The insoluble fraction in the present invention can be obtained, for example, by bursting the fungal cells of which cell wall has been substantially removed or at least partially removed. Further, a precipitate fraction obtainable by centrifuging the component thus obtained from bursting at about 100,000×g can also be used as the insoluble fraction.

Furthermore, the fungal antigen of the present invention may be a solubilized fraction extracted and separated from the insoluble fraction in the present invention. The solubilized fraction mainly contains antigenic soluble proteins. In addition, sugars and lipids may also be contained therein. The solubilized fraction can, for example, be sterilized by filtration in the purification step, thereby making it possible to prepare antigenic components, which are labile to sterilization procedures by heating or with organic solvents, with maintaining the activity in the solubilizing step. Such a solubilized fraction can be obtained by extraction and separation with a buffer containing a solubilizer, for example, a buffer containing a surfactant.

Furthermore, the fungal antigen of the present invention may be a fraction obtained by further purifying an insoluble fraction or solubilized fraction by a means of separation and purification appropriate for the purpose. For example, a fraction containing a molecule having binding ability to a sugar group-specific affinity medium is obtained by treating with the adsorbent a solubilized fraction from *Candida albicans* TIMM 1768 used as a starting material, and the fraction can also be used as the fungal antigen of the present invention. The sugar group-specific affinity medium includes, for example, immobilized concanavalin A (ConA) media. Because ConA binds to molecules containing α-D-mannopyranose, α-D-glucopyranose, or a sterically similar sugar residue thereof, components contained in the solubilized fraction can be further separated into some fractions on the basis of differences in the sugar residue contained in each component by using ConA-immobilized resin. For example, a ConA-binding fraction separable from the *Candida albicans* TIMM 1768 solubilized fraction (fraction having high content in proteins having ConA-binding sugar residues) exhibits sufficient protection activity against infection when administered to the mouse.

On the other hand, various fungal antigens of the present invention are present in fractions comprising molecules not having binding ability to sugar group-specific affinity media. In other words, the fungal antigen of the present invention also includes a fraction obtained as described above comprising molecules not having binding ability to sugar group-specific affinity media, and may include a fraction obtained by further purifying such a fraction. For example, by further subjecting a ConA-unbindable fraction derived from *Candida albicans* TIMM 1768 to ion exchange chromatography etc., purified fragments containing an antigenic protein having the partial amino acid sequence as shown by SEQ ID NO: 1 in Sequence Listing and a molecular weight of about 65,000 (SDS-PAGE, under reduced conditions); an antigenic protein having the partial amino acid sequence as shown by SEQ ID NO: 2 in Sequence Listing and a molecular weight of about 25,000 (SDS-PAGE, under reduced conditions); an antigenic protein having the partial amino acid sequence as shown by SEQ ID NO: 3 in Sequence Listing and a molecular weight of about 30,000 (SDS-PAGE, under reduced conditions); an antigenic protein having the partial amino acid sequence as shown by SEQ ID NO: 4 in Sequence Listing and a molecular weight of about 62,000 (SDS-PAGE, under reduced conditions); an antigenic protein having the partial amino acid sequence as shown by SEQ ID NO: 14 in Sequence Listing and a molecular weight of about 35,000 (SDS-PAGE, under reduced conditions); and an antigenic protein having the partial amino acid sequence as shown by SEQ ID NO: 15 in Sequence Listing and a molecular weight of about 55,000 (SDS-PAGE, under reduced conditions) can be obtained. The purified fraction or each isolated antigenic protein which is used as the fungal antigen of the present invention is useful in the therapy and diagnosis of diseases caused by fungi. These isolated antigenic proteins, in particular, are useful in identification of causative antigens etc. in diagnosis.

These antigenic proteins are derived from *Candida albicans* and possess vaccine activity against infectious diseases caused by *Candida albicans* or possess allergen activity useful in the prevention and therapy of allergic symptoms caused by *Candida albicans*. The term "vaccine activity," as used in the present specification, means that the vaccine prepared by a conventional method using the fungal antigen of the present invention exhibits a pharmacological action effective as a vaccine. The term "allergen activity" means that an abnormally high value is obtained in an IgE antibody titer measurement test against the fungal antigen of the present invention by RAST etc. using a serum from a patient with allergosis, or a positive reaction is shown in a skin test using the fungal antigen of the present invention.

Furthermore, in the present invention, functional equivalents possessing properties immunologically equivalent to those of isolated antigenic proteins as described above are also encompassed in the scope of the fungal antigen of the present invention. For example, functional equivalents of various strains of *Candida albicans*, and fungi of *Candida* other than *Candida albicans*, are also encompassed in the present invention. More specifically, among the above-described six kinds of antigenic proteins, the antigenic protein having a molecular weight of about 65,000 has homology with the dihydrolipoamide dehydrogenase (DLDH) of *Saccharomyces cerevisiae* localized in mitochondria; the antigenic protein having a molecular weight of about 25,000 has homology with the superoxide dismutase (SOD) of *Saccharomyces cerevisiae* localized in mitochondria; the antigenic protein having a molecular weight of about 30,000 has homology with the citrate synthase of *Saccharomyces cerevisiae*; the antigenic protein having a molecular weight of about 62,000 has homology with the vacuolar aminopeptidase I of *Saccharomyces cerevisiae*; and the antigenic protein having a molecular weight of about 35,000 has homology with malate dehydrogenase of *Saccharomyces cerevisiae*. Antigens having equivalent immunological properties, such as vaccine activity and/or allergen activity, to malate dehydrogenase are also encompassed in the present invention. The antigenic protein having a molecular weight of about 55,000 has the partial amino acid sequence as shown by SEQ ID NO: 15 in Sequence Listing, and the antigenic protein was identified as catalase based on the fact that the above partial amino acid sequence is identical with the amino acid sequence of 2nd to 31st residues starting from the N-terminal of the protein consisting of 487 amino acids encoded by a catalase gene CAT1 ["*Infection Immunity*," Vol. 66, 1953-1961 (1998)] which has been previously cloned. Incidentally, the reactivity of the protein encoded by CAT1 and anti-*Candida* serum has not been known, and the antigens having equivalent immunological properties, such as vaccine activity and/or allergen activity, to proteins encoded by CAT1 are also encompassed in the present invention.

The phrase "functional equivalent possessing immunologically equivalent properties," as used herein, is defined as a protein with substitution, insertion, deletion, or addition of one or more amino acids of which the immunological properties, such as vaccine activity and/or allergen activity, are equivalent to the above.

Also, an antigenic fragment can also be prepared based on an isolated antigenic protein. An antigenic fragment can, for example, be prepared by cleaving an isolated antigenic protein as the starting material by enzymatic digestion with a protease, such as lysyl endopeptidase or trypsin, or by chemical treatment with cyanogen bromide etc., and then isolating and purifying a fragment possessing the desired antigenicity by a known method for protein purification. It is also possible to produce an antigenic fragment by chemical synthesis using peptide synthesis technology, on the basis of the information on the chemical structure of the antigenic fragments. The antigenic fragment of the present invention includes fragments of a fungi-derived antigenic protein that cause immune responses in mammals, especially in humans, including for instance, minimal level of IgE stimulation, IgE binding, and induction of IgG and IgM antibody production, or T cell responses, such as proliferation, and/or lymphokine secretion and/or T cell anergy induction.

The antigenicity of an antigenic fragment can also be evaluated by in vitro tests, such as RAST, ELISA, and histamine release tests, in addition to skin tests and intradermal tests in human volunteers.

Incidentally, for the purpose of increasing fungal antigen stability and/or increasing desired reactivity, i.e., enhancing the induction of individual protective immunity, attenuating allergic reactions, or inactivating enzymes, for therapeutic purposes, and enhancing specific antigen-antibody binding for diagnostic purposes, it is possible to modify an antigenic protein or antigenic fragment to a derivative thereof, or to bind it with polyethylene glycol (PEG) using the PEG method [Wie et al., *Int. Arch. Allergy Appl. Immunol.*, Vol. 64, 84-99 (1981)]. Protein modifications include pyridylethylation, reduction, alkylation, acylation, chemical coupling to appropriate carriers, mild formalin treatment, and guanidine hydrochloride treatment.

Alternatively, based on the information of a partial amino acid sequence for the above isolated antigenic protein nucleic acids encoding the antigen can be isolated by PCR and the like. An example thereof is described as follows:

First, cDNA library is prepared from cells expressing a desired antigenic protein. Next, PCR is carried out with genomic DNA for the cell expressing the antigenic protein as a template, by using an oligonucleotide usable for an amplification primer which is designed based on the nucleotide sequence of the nucleic acid which is deduced to encode a partial amino acid sequence of an antigenic protein; and a suitable oligonucleotide capable of forming an amplification primer pair with the above oligonucleotide for the above nucleic acid. A DNA encoding the desired antigenic protein can be selected from the cDNA library by hybridization using a DNA fragment obtained by the above PCR. For example, a DNA having the nucleotide sequence as shown by SEQ ID NO: 7 in Sequence Listing encoding a protein having the amino acid sequence as shown by SEQ ID NO: 5 can be isolated by the above method using the amino acid sequence information as described by SEQ ID NO: 1 in Sequence Listing, cDNA library of *Candida albicans* TIMM 1768, and genomic DNA of *Candida albicans* TIMM 1768.

In addition, nucleic acids encoding the antigenic protein can be isolated by RT-PCR using RNA from cells expressing the desired antigenic protein and amplification primers designed based on nucleotide sequences of a nucleic acid, the sequence being deduced to encode a partial amino acid sequence, and the like. For example, a DNA having the nucleotide sequence of SEQ ID NO: 8 in Sequence Listing encoding a protein having the amino acid sequence as shown by SEQ ID NO: 6 in Sequence Listing can be isolated by the above method using an amino acid sequence information as described by SEQ ID NO: 2 in Sequence Listing and an RNA from *Candida albicans* TIMM 1768.

Incidentally, in the present invention, nucleic acids encoding a fungal antigen comprising a protein having the amino acid sequence as described by SEQ ID NO: 5 in Sequence Listing are not particularly limited to nucleic acids having the nucleotide sequence as shown by SEQ ID NO:7. Similarly, nucleic acids encoding a fungal antigen comprising a protein having amino acid sequence as shown by SEQ ID NO: 6 in Sequence Listing are not particularly limited to nucleic acids having the nucleotide sequence as shown by SEQ ID NO: 8 in Sequence Listing. Specifically, with regard to the codon designating an amino acid on a gene (triplet base combination), 1 to 6 kinds are known to exist for each kind of amino acids. Therefore, a large number of nucleic acids encoding an amino acid sequence can exist depending on the amino acid sequence. In nature, the nucleic acid is not stable, and it is not unusual that nucleic acid variations occur. A mutation on the nucleic acid may in some cases not cause a change of the amino acid sequence to be encoded (silent mutation). In this case, it can be said that different nucleic acids encoding the same amino acid sequence have been produced. Therefore, a possibility cannot be negated where even when a nucleic acid encoding a particular amino acid sequence is isolated, a variety of nucleic acids encoding the same amino acid sequence are produced with generation passage of the organisms containing the nucleic acids. Moreover, it is not difficult to artificially produce a variety of nucleic acids encoding the same amino acid sequence by means of various genetic engineering procedures.

For example, in the production of the protein by genetic engineering, when a codon used in the natural gene encoding the desired protein is low in usage in the host utilized, the amount of the protein expressed is sometimes low. In such a case, a high level expression of the desired protein is achieved by artificially converting the codon into another one of high usage in the host without changing the amino acid sequence encoded (for example, Japanese Examined Patent Publication No. Hei 7-102146). It is of course possible to artificially prepare a variety of genes encoding a particular amino acid sequence.

Furthermore, nucleic acids encoding the fungal antigen in the present invention encompass nucleic acids being capable of hybridizing to a nucleic acid comprising the entire sequence of the nucleotide sequence of SEQ ID NO: 5 or 6 in Sequence Listing, or a partial sequence thereof, and the peptide encoded by the above nucleic acid has a vaccine activity or an allergen activity equivalent to the fungal antigen of the present invention. As to the term "capable of hybridizing," the following conditions may be exemplified:

Specifically, a DNA-immobilized membrane is incubated with a probe at 50° C. for 12 to 20 hours in 6×SSC, wherein 1×SSC indicates 0.15 M NaCl, 0.015 M sodium citrate, pH 7.0, containing 0.5% SDS, 0.1% bovine serum albumin (BSA), 0.1% polyvinyl pyrrolidone, 0.1% Ficol 400, and 0.01% denatured salmon sperm DNA. After termination of the incubation, the membrane is washed, initiating at 37° C. in 2×SSC containing 0.5% SDS, and changing the SSC concentration to 0.1×SSC and the SSC temperature to 50° C., until a signal from the immobilized DNA becomes distinguishable from the background.

When the above nucleic acid is used, an antigenic protein can be prepared by genetic engineering procedure as a recombinant protein in *Escherichia coli*, yeast, fungus, mammalian cells, or the like. In addition, an antigenic fragment of the above antigenic protein can be prepared by genetic engineering procedure by the use of a partial portion of the above nucleic acid.

When the above gene information can be obtained, a functional equivalent of the antigenic protein can be obtained by modifying a structure of the antigenic protein by a known method using mutagenesis at a particular site on the nucleic acid encoding an antigenic protein. For example, substitution, insertion, deletion or addition of amino acid residues can occur by substitution, insertion, deletion or addition of one or more of bases for nucleic acids encoding a protein. Specifically, the fungal antigens comprising a peptide resulting from at least one of deletion, addition, insertion or substitution of one or more of amino acid residues in the amino acid sequence comprising an amino acid sequence as shown by SEQ ID NO: 5 or SEQ ID NO: 6 in Sequence Listing or a partial portion thereof, and the peptide having the vaccine activity or the allergen activity, which is a mutant of the antigenic protein of the present invention and an example of a functional equivalent, are also included in the scope of the present invention. In addition, a mutant retaining to have the biological activity can be selected.

The gapped duplex method [Wilfried, K. et al., *Nucleic Acids Research*, Vol. 12, 24, 9441-9456, (1984)], the deletion method [Celeste, Y. P. et al., *Gene*, Vol. 33, 103-119, (1985)], the PCR method [*Gene*, Vol. 102, 67-70, (1991)], the uracil DNA method [Thomas, A. K. et al., *Methods in Enzymology*, Vol. 154, 367-382, (1987)] and the cassette mutation method [James, A. W. et al., *Gene*, Vol. 34, 315-323, (1985)] and the like are known as the methods for preparing the mutant.

The toxicity of the fungal antigen of the present invention (Ca-LSP in Example 1) is low, so that no abnormalities are observed even when intravenously administered to the mouse at 20 mg/kg.

3. Process for Producing Fungal Antigen

A process for producing fungal antigen which is an insoluble fraction obtainable from fungal cells of which cell wall has been substantially removed or at least partially removed include, for example, a process comprising the steps of:

(1) obtaining living fungal cells;
(2) obtaining fungal cells of which cell wall has been substantially removed or at least partially removed;
(3) bursting the fungal cells of which cell wall has been substantially removed or at least partially removed; and
(4) obtaining an insoluble fraction.

Step (1)

Step (1) comprises obtaining living fungal cells. More specifically, step (1) comprises culturing a fungus in a culture medium suitable for its growth, and obtaining fresh living fungal cells.

First, fungal cultivation can be carried out under temperature and other conditions in which fungi can grow in a nutrient medium containing carbon sources, nitrogen sources, and other nutrient sources suitable for each fungus. As the nutrient media usually usable for fungal cultivation, Sabouraud medium, Potato-Dextrose medium, Czapek-Dox medium, malt medium, yeast nitrogen base glucose chemically defined medium, and the like can be widely used, and serum and/or serum albumin may be added as necessary. Also, there are some fungi of which growth is suited in media supplemented with olive oil or the like, like *Malassezia furfur*. Although the culturing temperature is usually from about 15° to about 45° C., some fungi show morphological changes depending on the culturing temperature (many of which are known as dimorphic fungi), and an appropriate selection of a culturing temperature is necessitated. For instance, in the case of *Candida albicans*, for which preferably employable culturing temperature is in the range from 25° to 37° C., yeast-phase growth takes place at about 30° C. when cultured in usual media, whereas mycelial-phase growth is likely to take place around 37° C. For dimorphic fungi, culturing conditions may be altered according to the purpose, since changes also occur in cell wall components, and protein components, such as intracellular proteins, including membrane proteins. Many fungi aggregate or form lumps of cells, to give a nonuniform cell suspension, under ordinary culturing conditions, in which case the cell wall lytic enzyme etc. cannot sufficiently act on the fungus in the subsequent step. Therefore, in order to obtain a cell suspension as uniform as possible, the culturing method may be modified. In the case of *Aspergillus fumigatus*, for example, this problem can be solved by increasing the salt concentration by adding 0.5 to 1 M NaCl, or the like to a medium. Also, the fungus can be exemplified by the fungi described above.

Step (2)

Step (2) comprises obtaining fungal cells of which cell wall has been substantially removed or at least partially removed. Although the cell wall may be removed to an extent to at least show sensitivity to osmotic pressure, it is preferable that the cell wall is further removed to an extent of protoplast formation. Therefore, the fungal cells of which cell wall has been substantially removed or at least partially removed are preferably the protoplasts or spheroplasts of the fungal cells.

The fungal cells of which cell wall has been substantially removed or at least partially removed, can, for example, be obtained by allowing a cell wall lytic enzyme to act on the fungal cells, or by physically treating the fungal cells. The cell wall lytic enzyme treatment and the physical treatment may be used in combination.

There are various cell wall lytic enzymes known to date, commercial products including ZYMOLYASE (manufactured by Seikagaku Corporation), Lyticase (manufactured by Sigma), Yatalase (manufactured by Ozeki Corporation-Takara Shuzo Co., Ltd.), Chitinase (manufactured by Takara Shuzo Co., Ltd.), *Trichoderma* Lysing Enzyme (manufactured by Novo-Sigma), snail intestinal digestion enzyme β-glucuronidase (manufactured by Sigma), and Laminariase (manufactured by Sigma). These enzymes comprise lytic enzymes for various cell wall polysaccharides (chitin, β1,3-glucan, mannan, galactomannan, xyloglucan, etc.), many of which further contain proteases.

In order to lyse the cell wall of fungal cells and prepare naked cells sensitive to osmotic pressure, e.g., protoplasts, firstly fresh cells obtained by culturing are washed, and then suspended in a hypertonic buffer containing 0.8 to 1.5 M sorbitol, mannitol, or NaCl. A required amount of the cell wall lytic enzyme at temperature, buffer, and pH conditions suitable for the enzyme is acted on the suspension for 10 minutes to several hours to remove the cell wall. In this operation, the cell wall can be more completely removed by allowing to act a protease thereon in some cases. Some fungi do not necessitate protease action, in which case a protease inhibitor, such as PMSF or pepstatin, may be added.

The physical treatment can, for example, be carried out by suspending subject cells in a hypertonic buffer such as a 2.5 M sucrose solution to cause plasmolysis, and cutting off the cell wall with a knife.

Step (3)

Step (3) comprises bursting the fungal cells of which cell wall has been substantially removed or at least partially removed obtainable in step (2). Methods for cell bursting include, for example, ultrasonication, French press treatment, and hypotonic solution treatment utilizing differences in osmotic pressures. The bursting with hypotonic solution treatment can be carried out by sufficiently washing cells with a hypertonic solution, and then suspending the cells in a hypotonic solution, i.e., physiological saline or a buffer of low ionic strength (e.g., physiological saline in the case of *Candida albicans* TIMM 1768). The usable buffers include, for example, phosphate buffers and citrate buffers, each having a pH of 5 to 8. In order to recover the cell organelles as intact as possible, ionic strength can be selected. For example, in order to prepare mitochondria in a condition ensuring similar functions to that in the cells, cells of which cell wall has been substantially removed or at least partially removed are burst by treating the cells by means of ultrasonic, a Waring blender, a French press, or the like in a buffer containing 0.5 to 0.6 M sorbitol or 0.25 M sucrose to thereby obtain mitochondria in a state having similar functions to the cells.

Step (4)

Step (4) comprises obtaining an insoluble fraction.

The component obtainable by bursting obtained in step (3) is centrifuged or filtered to yield a precipitate or residue, which is taken as the insoluble fraction. The component obtained by bursting may be further finely disintegrated using ultrasonic or glass beads as occasion demands.

Although centrifugal conditions for obtaining the insoluble fraction are not particularly limited, it is preferable that centrifugation is carried out at about 100,000×g or less, more preferably 10,000×g or less, and that the centrifugation time is from 10 minutes to 3 hours.

Components recoverable as precipitates by centrifugation at 10,000×g or less are cytoplasmic membranes, and cell organelles, such as mitochondria, nuclei, lysosome, and vacuoles. Cytoplasmic membrane proteins and cell organelle membrane proteins can be obtained as precipitates in which the protein is bound to the membrane.

When centrifuged at 100,000×g for about one hour, ribosome is also recovered as a precipitate, which may be contained in the insoluble fraction. Centrifugal conditions may be altered to separate individual cell organelles to some extent. For example, centrifugation at about 1,000×g allows to separate nuclei. Also, the above-mentioned cell organelles can be separated and purified by density gradient centrifugation using sucrose etc. It is also possible to recover the insoluble fraction by filtration, and to classify it according to its particle size to some extent.

Because the insoluble fraction thus obtained is from the fungal cells of which cell wall has been substantially removed or at least partially removed, such as the protoplasts or spheroplasts of the fungal cells, the amount of cell wall components which can be contained in the insoluble fraction is low. For example, the amount of cell wall component contained in the insoluble fraction of the present invention can be quantified by utilizing an antigen-antibody reaction in which the cell wall component is taken as the antigen. More specifically, as described in Examples detailed below, when the fungal cells used are *Candida albicans* TIMM 1768, for example, the serotype A mannan in the insoluble fraction can be quantified using serum factor No. 1 (manufactured by IATRON LABORATORIES, Inc.), which is an anti-*Candida* serum. The amount of serotype A mannan thus determined is preferably not greater than the detection limit (0.5 mg/ml).

The insoluble fraction obtainable as described above can also be washed and sterilized with an organic solvent, such as ethanol, isopropanol, phenol, or acetonitrile, or sterilized by heat treatment.

The insoluble fraction in the present invention can be obtained as described above. Also, in the present invention, a solubilized fraction obtainable by extracting and separating the insoluble fraction also serves as a fungal antigen. The solubilized fraction can, for example, be obtained by a process comprising the following steps:

(1) obtaining living fungal cells;
(2) obtaining fungal cells of which cell wall has been substantially removed or at least partially removed;
(3) bursting the fungal cells of which cell wall has been substantially removed or at least partially removed;
(4) obtaining an insoluble fraction; and
(5) extracting and separating a solubilized fraction from the insoluble fraction.

In the present invention, the solubilized fraction can be further separated and purified in step (6) by conventional means of separation and purification according to the purpose, as desired.

Of the above steps, steps (1) through (4) are the same as those for the process for producing an insoluble fraction. It should be noted, however, that although the cell wall component in the insoluble fraction usable in these steps is preferably removed to an extent that the insoluble fraction can be used clinically, this extent needs not always be the same level as the extent where the insoluble fraction per se is used as the fungal antigen. This is because the cell wall of fungal cells is rich in glucan, chitin, or the like, some of which components are insoluble, for instance, by surfactants and can be removed in the subsequent step comprising obtaining a solubilized fraction. Steps (5) and (6) will be hereinafter described.

Step (5)

Step (5) comprises extracting and separating a solubilized fraction from the insoluble fraction. For the extraction and separation, those generally used in methods for solubilization can be used. The solubilizers include, for example, salts, such as NaCl and KCl; chelating agents, such as EDTA; organic solvents, such as butanol; and buffers in which a protein denaturant, such as urea, is dissolved therein, it is preferable from the viewpoints of solubilized component stability and extraction efficiency that a buffer containing a surfactant is used. If satisfactory extraction effects cannot be obtained, the above-mentioned organic solvents and protein denaturants may be used in combination. Generally, a solubilized fraction can be obtained by suspending the insoluble fraction obtainable in step (4) in a buffer containing an appropriate solubilizer, such as a surfactant, for a given period of time, and then removing the insoluble components by centrifugation and/or filtration. The term "solubilized fraction," as used herein, is understood to include water-soluble components accompanying the insoluble fraction, for example, intraorganellar water-soluble components, and/or components solubilized by solubilizing treatment, including, for example, cytoplasmic membrane proteins and lipids. Also, when using a clinically usable surfactant, the solubilized fraction per se can be used as a fungal antigen without removing the surfactant.

The surfactant usable in solubilization of the membrane proteins etc. contained in the insoluble fraction usable in the present invention is preferably octylthioglucoside, Lubrol PX, Triton X-100, sodium lauryl sulfate (SDS), Nonidet P-40, and the like. The clinically usable surfactants include ionic (anionic, cationic, amphoteric) surfactants (e.g., alkyl sulfonates, benzalkonium chlorides, and the like) and non-ionic surfactants (e.g., polyoxyethylene hydrogenated castor oils, polyoxyethylene sorbitol fatty acid esters, polyoxyethylene sorbitan fatty acid esters, polyoxyethylene glycerol fatty acid esters, polyethylene glycol fatty acid esters, polyoxyethylene alkyl phenyl ethers, and the like). The surfactant used in the present invention is preferably a nonionic surfactant. The polyoxyethylene hydrogenated castor oils include, for example, NIKKOL HCO-40, HCO-50, and HCO-60 (manufactured by Nikko Chemicals) and Uniox HC-40, HC-50, and HC-60 (manufactured by NOF Corporation).

The polyoxyethylene sorbitol fatty acid esters include, for example, NIKKOL GO-430, GO-440, GO-460, GL-1, Atlox 1045A, 1196, G-1045, and G-1441 (manufactured by Kao Atlas). The polyoxyethylene sorbitan fatty acid esters include TWEEN 20, TWEEN 40, TWEEN 60, TWEEN 80, EMASOL 1130, EMASOL 3130, NIKKOL TL-1010, TP-10, TS-10, and the like. The polyoxyethylene glycerol fatty acid esters include, for example, NIKKOL TMGS-15, TMGS-5, and the like. The polyoxyethylene glycol fatty acid esters include, for example, NIKKOL MYL-110, MYS-10, and the like. The polyoxyethylene alkyl phenyl ethers include NIKKOL NP-10, EMULGEN 810, and the like. Incidentally, in the case where surfactants such as SDS having a high protein solubilizing ability but limited for their clinical use are used, the antigenic components and the surfactant may be separated by a subsequent appropriate treatment as occasion demands.

From the viewpoint of sustaining antigenicity, etc., it is a matter of course to select an optimum kind of a surfactant and an optimum concentration thereof for soluble components. Generally, the surfactant is effective as long as the concentration of the surfactant is equal to or higher than the level at which the surfactant forms a micelle when dissolved in an aqueous solvent, i.e., equal to or higher than the critical micellar concentration (hereinafter referred to as "CMC"). The surfactant is preferably used at concentrations of the CMC or higher and up to 10 times the CMC, with especially good action when solubilized at concentrations from the CMC to 5 times the CMC. The buffers include phosphate buffers and Tris-HCl buffers.

The solubilization is usually carried out by allowing the insoluble fraction to stand, or stirring the insoluble fraction, at a low temperature of about 4° C. for one hour to overnight. In this operation, a protease inhibitor may be added. The solubilized fraction can, for example, be obtained as a supernatant of the centrifuged solubilization treatment liquid at about 100,000×g for about one hour, or as a filtrate of the filtered solubilization treatment liquid. It is also possible to remove the solubilizer used for solubilization by dialyzing the supernatant or filtrate against a solubilizer-free buffer or a buffer containing a clinically usable surfactant; or adding an organic solvent such as ethanol or acetone, allowing to make the protein insoluble and form sedimentation, and collecting the sedimentation by centrifugation, or the like. The solubilized fraction may also be washed and sterilized with an organic solvent, such as ethanol, isopropanol, phenol, or acetonitrile, or sterilized by heat treatment.

In addition, when the solubilized fraction is dialyzed against a solubilizer-free buffer, a portion of hydrophobic components, including lipids, is obtained as precipitates. These precipitate components and solution components are all encompassed in the scope of the solubilized fraction in the present specification.

In the present invention, as step (6), the solubilized fraction may be further purified by conventional means of separation and purification according to its purpose, including, for instance, means of separation and purification based on differences in component affinity, charged states, molecular weights, hydrophobicity, and the like as desired. For example, the solubilized fraction can be purified by fractionation based on differences in the sugar residues contained in the glycoprotein with a sugar group-specific affinity medium. The sugar group-specific affinity media include, for example, immobilized lectin media. In particular, preference is given to ConA-bound resins for the separation of a component having a ConA-binding sugar residue (α-D-glucose residue and α-D-mannose residue of which C-3, C-4, and C-6 hydroxyl groups are unsubstituted), e.g., a glycoprotein, which can be found in many of fungi, rich in ConA-binding mannose residues. For purification, it is desirable to use a buffer according to its purpose, and a surfactant, an organic solvent, and the like may be also added. The degree of purification may be increased using an ion exchange resin or gel filtration carrier.

Also, in the present invention, the fungal antigen of the present invention can easily be produced by general genetic engineering techniques using a nucleic acid encoding the fungal antigen of the present invention described above.

4. Biologic Products

The biologic product of the present invention contains the fungal antigen described above as an active ingredient. A biologic product is a vaccine or similar preparation derived from a pathogenic microorganism of an infectious disease, and used to diagnose, prevent or treat a disease or a disorder. In the present invention, the fungus is used as the starting material therefor. Besides, the biologic product containing therapeutic sera or the like obtainable by using the antigen of the present invention is also included. Among them, the fungal antigen of the present invention, which contains a large number of kinds of fungal proteins, is capable of inducing acquired immune in vertebrates, so that it can particularly preferably be used in a vaccine composition. In other words, the vaccine preparation of the present invention, having protective immunity against infection or therapeutic effects against a mycotic infectious disease in vertebrates, contains the fungal antigen described above as an active ingredient. The fungal antigen contained in the biologic product or vaccine composition of the present invention as an active ingredient can, for example, be obtained by the production method described above. Incidentally, in the present specification, a vaccine composition is simply referred to as a vaccine in some cases.

When the fungal antigen of the present invention is used as a vaccine composition, in order to get more potent humoral and/or cellular immunity, it is preferable to administer the fungal antigen in the form of preparation of a suspension or solution containing an adjuvant as described below. Although the adjuvant is usually administered together with the antigen, the adjuvant may be administered before or after antigen administration. The adjuvants suitable for vaccination for mammals include complete or incomplete Freund's adjuvant; gels made of inorganic substances such as aluminum hydroxide and alum; surfactants, such as lysolecithin, dimethyloctadecyl ammonium bromide and lysolecithin; polyanions, such as dextran sulfate and poly-IC; peptides, such as muramyl dipeptide and tuftsin; Monophosphoryl Lipid A (MPL) manufactured by Ribi; TiterMax, manufactured by CytRx; cholera toxin (CT); B subunit of CT; heat-labile toxin (LT), without being limited thereto. The antigen can also be administered by incorporating it in a liposome or other microcarriers. As a matter of course, antigens of some different fungi can also be used in admixture, whereby protective immunity against a plurality of mycotic infectious diseases is induced. The vaccine composition of the present invention may be used in combination with antifungal agents, such as fluconazole and amphotericin B, and β-lactam antibiotics and other various antibacterial antimicrobial agents. The vaccine composition of the present invention exhibits an additively or geometrically enhanced effectiveness when used in combination with an antifungal agent.

Vertebrates are fish, amphibians, reptiles, birds, humans, and mammals except humans, which produce antibodies in reaction with antigens, so that all vertebrates are capable of reacting with vaccines. Although vaccines are generally applied to mammals, such as humans or domestic animals, vertebrates, e.g., fish cultured for commercial purposes, are encompassed in the scope of the present invention, as long as they possess the above-described properties.

As the route of administration, the fungal antigen of the present invention may be administered orally, transmucosally (e.g., nasally, intravaginally), percutaneously (subcutaneously or intracutaneously), or intravenously. Representative initial doses are 0.001 to 5 mg/kg body weight as an amount of protein, and depending upon to the degree of prevention or therapy required the dose can be increased, or the number of administration can be increased.

When an insoluble fraction or a solubilized fraction derived therefrom, which is the fungal antigen of the present invention, is administered, potent cellular immunity and/or humoral immunity can be induced, whereby fungal infection can be prevented or treated. The protective effects and therapeutic effects can be induced not only against the fungus of interest for protection or therapy but also against other fungi though with some insufficiency. This is presumably due to the fact that commonness of antigens among fungi and/or activation of the immune system induce release of superoxide anions, nitric oxide, and various cytokines, which possess a broad spectrum of antimicrobial activity.

In addition, the present invention provides 1) a pharmaceutical composition for inducing protective immunity against fungi or exhibiting therapeutic effects by administering to individuals, characterized in that the pharmaceutical composition contains the fungal antigen described above, or a fungal antigen produced by the process described above; 2) a vaccine composition for inducing protective immunity against fungi or exhibiting therapeutic effects by administering to individuals, characterized in that the vaccine composition contains the fungal antigen described above, or a fungal antigen produced by the process described above; 3) a method of stimulating immune responses against fungi in a vertebrate, comprising the step of administering the above vaccine composition; and 4) a method of stimulating immune responses against fungi in a vertebrate, wherein proliferation of fungi used in the preparation of the vaccine composition and/or fungal strains closely related thereto is suppressed by the immune responses in a vertebrate to which the vaccine composition is administered, to prevent or treat diseases caused by the fungi.

The fungal antigen of the present invention can be used in the form of a biologic product, such as a cytokine releasing agent, and an allergen composition usable for desensitization therapy for allergoses and other purposes, as well as the above-described vaccine composition. Further, the fungal antigen of the present invention can also be used for in vivo diagnosis and/or laboratory diagnosis for determination of past history of infection by skin reactions, allergosis diagnosis by scratch tests, and for other purposes. Preparations used for laboratory diagnosis include, for example, immunological diagnostic agents, such as microtiter reagents, latex agglutination reagents, immunonephelometric reagents, and enzyme immunoassay reagents.

When used to an individual, the cytokine releasing agent of the present invention can be used in the form of a lyophilized powder or an appropriate salt solution or suspension, or a suspension or solution containing the above-described adjuvant. The cytokine releasing agent can also be used as a therapeutic agent for a disease on which the released cytokine is effective. For example, when the cytokine released is IFN-γ, the cytokine releasing agent can be used for a therapeutic agents for cancers, bacterial infectious diseases, and allergoses.

As the route of administration, it may be administered percutaneously (subcutaneously or intracutaneously), nebulized via intrapulmonary, administered transmucosally (e.g., via nose, eye, vagina, or the like), orally, subglossally, or intravenously. For example, a representative dose for treating cancer is 0.02 µg to 1 mg/kg per administration in the case of humans, and depending upon to the diseases treated and purposes required, the dose can be increased, or the number of administration can be increased. For example, the dose can be increased to a level of about 100 mg/kg per administration.

When the allergen composition of the present invention is administered to a patient for the purpose of preventing or treating allergosis, the allergen composition can be used in the form of an appropriate salt solution or suspension, and may be supplemented with polyethylene glycol or phenol. Further, it can also be administered as the suspension or solution containing an adjuvant usable for making vaccine preparations for mammals as described above. The adjuvant can be usually administered together with an antigen, and it may be given before or after antigen administration. The antigen can also be administered by incorporating it in a liposome or other microcarriers. As a matter of course, an insoluble fraction or solubilized fraction thereof can be mixed with similar fractions from some different fungi, or also mixed with commercially available fungal allergen extracts, various allergen extracts, such as those of house dusts and *Cryptomeria japonica*, and/or with purified allergens. By the use of the mixture, desensitization immunity against a plurality of allergens can be induced in patients with allergoses sensitive to a plurality of allergens.

As the route of administration, it may be administered percutaneously (subcutaneously or intracutaneously), nebulized via intrapulmonary, administered transmucosally (e.g., via nose, eye, vagina, or the like), orally, subglossally, or intravenously. A representative initial dose for treating depends upon the route of administration, and is, for example, 0.2 ng to 0.1 mg/kg per administration, and depending upon the degree of prevention and therapy required the dose can be increased, or the number of administration can be increased.

In addition, the present invention provides 1) an allergen composition for preventing allergoses against fungi or exhibiting therapeutic effects by administering to individuals, characterized in that the allergen composition contains the fungal antigen described above, or a fungal antigen produced by the process described above; 2) a method of suppressing allergic reaction to fungi in a vertebrate, comprising the step of administering the allergen composition; and 3) a method of suppressing allergic reaction to fungi in a vertebrate, wherein allergoses caused by fungi used in the preparation of the allergen composition and/or fungal strains closely related thereto are prevented or treated by the immune responses in a vertebrate to which the allergen composition is administered.

When the fungal antigen of the present invention is used in an individual for the purpose of in vivo diagnosis, e.g., in inhalation challenging test, skin test, or nasal or eye mucosal test, it can be used in the form of a lyophilized powder or an appropriate salt solution or suspension, and polyethylene glycol and/or phenol may be added thereto. For patch tests, it is possible to use a solution of the above-mentioned antigenic component in a mixture of white petrolatum as a base material supplemented with a surfactant, such as sodium lauryl sulfate.

The fungal antigen of the present invention can also be used for laboratory diagnoses, e.g., diagnostic methods based on antigen-antibody reactions, such as agglutination, precipitation reaction, and neutralization reaction; diagnostic methods using labeled antibody; histamine release test; lymphocyte transformation test; and leukocyte migration inhibition test. For example, when used as an antigen for IgE antibody titer, the above-described antigen component can be used by immobilizing it on a solid phase, such as a paper disc, cellulose sponge, or microplate.

The present invention also provides 1) a diagnostic composition for a disease caused by fungi, characterized in that the diagnostic composition contains the fungal antigen described above, or a fungal antigen produced by the process described above; and 2) a method for diagnosing a disease caused by fungi in a vertebrate, comprising using the diagnostic composition above.

Vertebrates which are subjects in the present invention are fish, amphibians, reptiles, birds, humans, and mammals except humans, which produce antibodies in reaction with antigens, so that all vertebrates are capable of reacting with antigens. Although the fungal antigens of the present invention are generally applied to mammals, such as humans or domestic animals, vertebrates, e.g., fish cultured for commercial purposes, are encompassed in the scope of the present invention, as long as they possess the above-described properties.

EXAMPLES

The present invention will be described concretely by the working examples, without intending to limit the scope of the present invention to these examples.

Example 1

Preparation of Cell Fraction and Insoluble Fraction of *Candida albicans* Cells

1) Preparation of protoplast cells: A platinum loopful of *Candida albicans* TIMM 1768 in Sabouraud agar slant culture was inoculated to an YPD medium (1% by weight yeast extract, 2% by weight polypeptone, 2% by weight glucose) in a test tube. After shaking culture at 30° C. for 24 hours, a portion of the culture was transferred to the YPD medium in an Erlenmeyer flask and subjected to shaking culture overnight at 35° C. The culture obtained was centrifuged at 2,000×g for 10 minutes to harvest the cells. The cells obtained were of an yeast phase. The cells were washed once with sterile water, and then washed once with an SSB solution (50 mM phosphate buffer, pH 7.5, containing 0.8 M sorbitol). After the cells were again suspended in an appropriate volume of the SSB solution, an SSB solution containing 100 mM EDTA in a volume of one-eighth that of the above SSB solution, and an appropriate volume of 2-mercaptoethanol were added thereto, followed by gentle shaking. Subsequently, to this suspension was added ZYMOLYASE 20T (manufactured by Seikagaku Corporation) to make up a final concentration of 0.3 mg/ml, followed by gentle shaking at 35° C. for one hour. Further, *Trichoderma* Lysing Enzyme (manufactured by Sigma) was added to make up a final concentration of 1 mg/ml, followed by gentle shaking at 35° C. for one hour. The suspension obtained was centrifuged at 2,000×g for 10 minutes to harvest the protoplast cells. The cells were sufficiently washed with the SSB solution and subjected to cell fractionation.

2) Subcellular fractionation from protoplast cells and preparation of antigen solutions: To the protoplast cells obtained as described above was added sterile physiological saline to make up a cell density of about $4 \times 10^9$ cells/ml, followed by sufficient stirring, after which the mixture was allowed to stand on ice for 10 minutes. After having confirmed that the protoplast cells were burst, the mixture was centrifuged at 10,000×g for 30 minutes, and the precipitate obtained was taken as an insoluble fraction (hereinafter referred to as "Ca-LSP"). The centrifugal supernatant was further centrifuged at 100,000×g for 60 minutes. The precipitate obtained was taken as a ribosome fraction (hereinafter referred to as "HSP"), and the centrifugal supernatant as a soluble fraction (hereinafter referred to as "HSS," wherein HSP90 and enolase were contained in this fraction). After suspending the Ca-LSP in the physiological saline again, the Ca-LSP was subjected to ultrasonic treatment, and then sterilized in a boiling water bath for five minutes, to yield an LSP antigen solution containing a membrane protein, and the like. The HSP was also suspended in the physiological saline to make up an appropriate protein concentration, and this suspension was taken as an antigen solution. The HSS was also assayed for protein concentration, and an appropriate volume was taken as an antigen. The Ca-LSP antigen solution obtained by treating the cells obtained from a 2-liter culture as described above had a protein concentration of 2.3 mg/ml, wherein the amount of protein was quantified by using bicinchoninic acid (BCA) reagent with BSA as a standard).

Figure 1B:
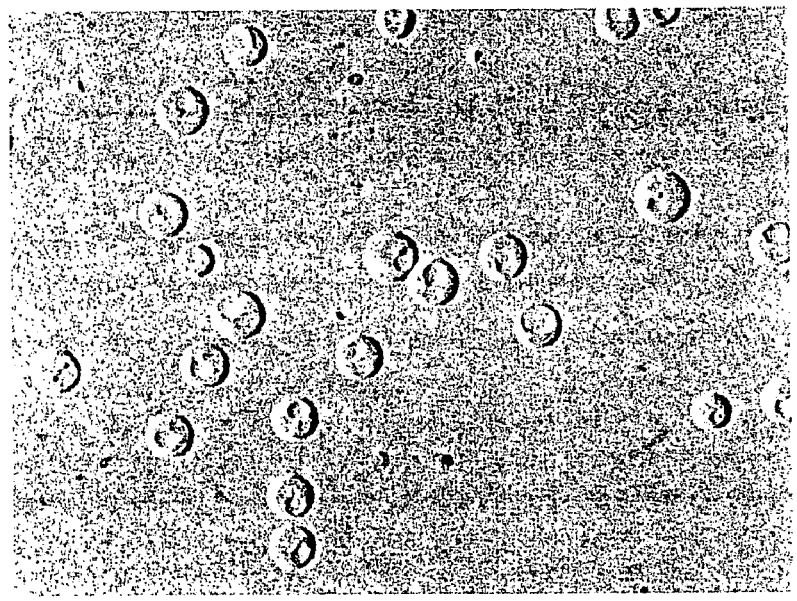
Figure 2A:
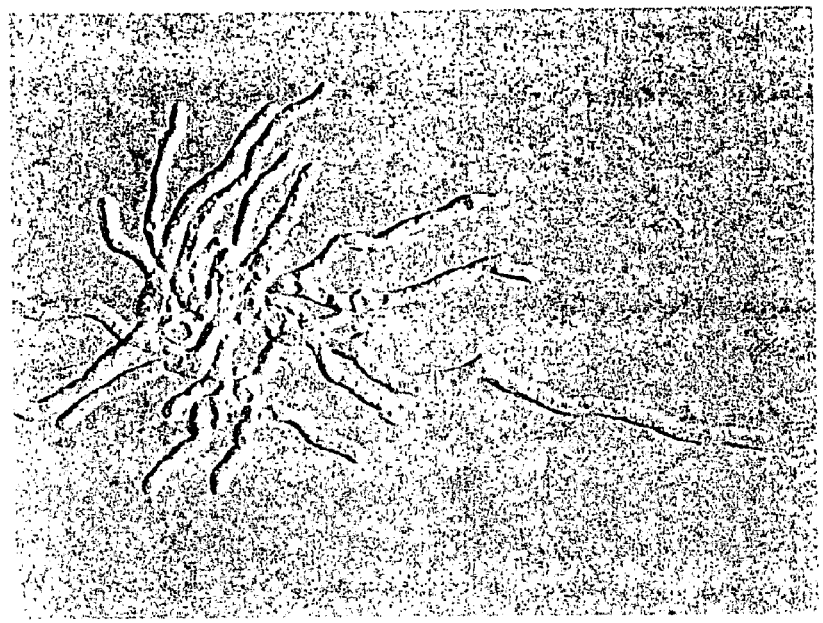
FIG. 2 is figures showing morphologies before and after cell wall removal from *Aspergillus fumigatus* cells, the figures being taken at a magnification of ×400 using a differential interference microscope (manufactured by NIKON Corporation), wherein A shows cells before cell wall removal, and B after cell wall removal.
Figure 2B:
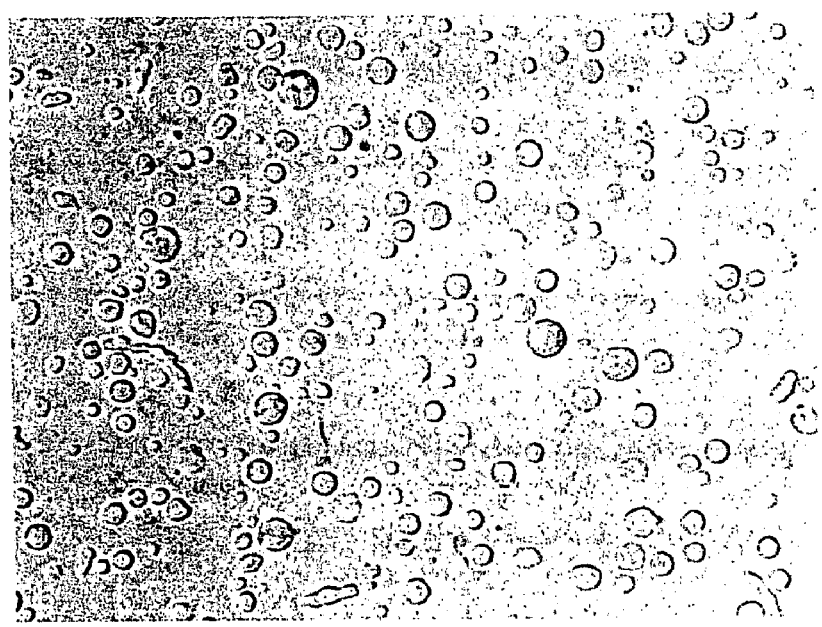

3) Confirmation for extent of cell wall removal of fungal cells: The extent of cell wall removal was confirmed by microscopic observation of cell morphology, by counting the number of living cells after bursting in physiological saline, and by a quantitation based on inhibition of agglutination with a serum factor by the antigen. In the case of *Candida albicans* or *Aspergillus fumigatus* cells, for example, when the cell wall was removed by the above-described method, marked changes in morphologies took place (FIGS. 1 and 2). Also, the protoplast cells prepared by the above-described method were burst in physiological saline, and living cells contained therein accounted for less than 1%. When 100 μl of the Ca-LSP antigen solution prepared above was spread over the YPD agar medium and cultured at 30° C. for four days, no *Candida albicans* cell colonies appeared, demonstrating that the living cells were not present in the Ca-LSP antigen solution. No colonies appeared from the HSP antigen solution or the HSS antigen solution.

On the other hand, serum factor No. 1 (manufactured by IATRON LABORATORIES, Inc.), an anti-*Candida* serum, causes to agglutinate cells of *Candida albicans* TIMM 1768 (serotype A). With inhibitory activity to this agglutination, the remaining amount of the cell wall components contained in the insoluble fraction was quantified as the amount of the cell wall mannan, a constituent component. The comparative control for cell wall mannan used was the Allergen Scratch Extract "Torii" *Candida* (manufactured by Torii Pharmaceutical Co., Ltd.), a commercially available *Candida* allergen extract.

As positive controls, serotype A mannan purified by the method of Kobayashi et al. [Kobayashi, H. et al., *Arch. Biochem. Biophys.* Vol. 272, 364-375 (1989)] from *Candida albicans* J-1012 strain (serotype A) was used in solutions at various concentrations. Although the commercially available *Candida* allergen extract (protein concentration: about 0.4 mg/ml) contained 4.5 mg/ml of serotype A *Candida albicans* cell wall mannan (hereinafter simply referred to as "serotype A mannan"), Ca-LSP (protein concentration: about 2.3 mg/ml) did not inhibit its agglutination, which clarified that the content of the serotype A mannan in the antigenic component of the present invention was not more than the detection limit by the method of 0.5 mg/ml. In other words, the fungal antigen of the present invention was found to have a high protein content and a cell wall mannan content of not more than the detection limit according to the method described above. Thus, it was shown to be clearly different from the conventional allergen extract.

The Ca-LSP antigen solution obtained was assayed for neutral sugar, lipid, and nucleic acid contents, and a portion thereof was taken and lyophilized, and then weighed. As a result, about 130 mg of the lyophilized residue (23 mg protein, 2 mg neutral sugars, 8 mg lipids, 90 mg NaCl as calculated, small amounts of nucleic acids and water as other components) was contained in 10 ml of the Ca-LSP antigen solution.

Example 2

Preparation of Insoluble Fraction of *Aspergillus fumigatus*

1) Preparation of insoluble fraction of *Aspergillus fumigatus* (Af-LSP) (1): Physiological saline containing 0.1% by weight of Tween 80 was added to a Sabouraud dextrose agar slant culture of *Aspergillus fumigatus* TIMM 1776 to prepare a spore suspension. A portion of the suspension was transferred to a Potato-Dextrose medium (manufactured by Difco) in an Erlenmeyer flask and subjected to shaking culture overnight at 30° C. The obtained culture was filtered with a glass filter to harvest mycelium. The mycelium was suspended in 10 mM phosphate buffer, pH 6.0, containing 0.8 M NaCl, and Yatalase (manufactured by Takara Shuzo Co., Ltd.) was added thereto to make up a final concentration of 10 mg/ml, followed by gentle shaking at 30° C. for four hours. The suspension obtained was filtered with a glass filter to harvest the protoplast cells.

The cells were washed twice with 0.8 M NaCl. Thereafter, to the protoplast cells obtained was added sterile physiological saline to make up a cell density of $1 \times 10^8$ cells/ml to be burst. An insoluble fraction was harvested by centrifuging the solution at 10,000×g for 30 minutes. After suspending the insoluble fraction in the physiological saline again, the insoluble fraction was subjected to ultrasonic treatment, and then sterilized in a boiling water bath for five minutes, to yield an insoluble fraction of *Aspergillus fumigatus* Af-LSP, the antigen solution No. 1 (protein concentration: about 0.9 mg/ml).

2) Preparation of insoluble fraction of *Aspergillus fumigatus* (Af-LSP) (2): A portion of a spore suspension prepared in the same manner as in the above item 1) was transferred to a Potato-Dextrose medium (manufactured by Difco) containing 0.8 M NaCl in an Erlenmeyer flask and subjected to shaking culture overnight at 30° C. The turbidity of the culture was of the same level as that of item 1). The obtained culture was filtered with a glass filter to harvest mycelium. The mycelium was suspended in 10 mM phosphate buffer, pH 6.0, containing 0.8 M NaCl. To the suspension were added Yatalase (final concentration: 10 mg/ml), *Trichoderma* Lysing Enzyme (final concentration: 3 mg/ml), and ZYMOLYASE 20T (final concentration: 1 mg/ml), followed by gentle shaking at 30° C. for two hours. The cell suspension obtained was filtered with a glass filter, and the protoplast cells were harvested from the filtrate. The number of the protoplast cells was counted, and as a result, it was found that the count of the protoplast cells was about twice that of the same volume of culture obtained in item 1) above. Therefore, it was clarified that the yield of protoplast cells was improved by the use of this culture method. The cells were washed twice with 0.8 M NaCl, and the obtained protoplast cells were treated in the same manner as in item 1) above, to yield an insoluble fraction of *Aspergillus fumigatus* Af-LSP, the antigen solution No. 2.

Example 3

Preparation of Insoluble Fraction of *Crytococcus neoformans* (Crn-LSP)

A platinum loopful of *Cryptococcus neoformans* TIMM 0354 in Sabouraud dextrose agar slant culture was inoculated to the YPD medium in an Erlenmeyer flask, followed by shaking culture at 30° C. overnight. The culture obtained was centrifuged to harvest the cells. The cells were washed once with sterile water, and then suspended in 100 mM citrate buffer, pH 5.8, containing 1 M sorbitol and 100 mM EDTA. *Trichoderma* Lysing Enzyme was added thereto to make up a final concentration of 5 mg/ml, followed by gentle shaking at 37° C. for one hour. The suspension obtained was centrifuged at 2,000×g for 10 minutes to harvest the protoplast cells. After the cells were washed with the above hypertonic buffer, sterile physiological saline was added to suspend the protoplast cells to make up a concentration of $1 \times 10^8$ cell/ml to be burst. The suspension was centrifuged at 10,000×g for 30 minutes to harvest an insoluble fraction. After suspending the insoluble fraction in the physiological saline again, the insoluble fraction was subjected to ultrasonic treatment, sterilized in a boiling water bath for five minutes, and then centrifuging at 10,000×g for 30 minutes, to yield an insoluble fraction. The insoluble fraction was taken as an insoluble fraction of *Cryptococcus neoformans*, Crn-LSP antigen solution (protein concentration: about 2.9 mg/ml).

Example 4

Preparation of Solubilized Fraction from *Candida albicans* Insoluble Fraction Ca-LSP To 100 ml of the Ca-LSP antigen solution obtained in Example 1 (protein concentration: 2.3 mg/ml) was added 100 ml of a 40 mM bis-Tris buffer (pH 6.5) containing 100 mM octylthioglucoside. After stirring the mixture overnight at 4° C., the mixture was centrifuged at 100,000×g for one hour, to yield 200 ml of a solution of a 50 mM octylthioglucoside-solubilized fraction (Ca-LSP-S) as the supernatant (protein concentration: 0.4 mg/ml). A 100 ml portion of this solution was concentrated by ultrafiltration (cutoff molecular weight: 10,000), and the concentrate was then dialyzed against phosphate-buffered physiological saline to remove the octylthioglucoside. This dialyzate was further filtered using a membrane filter with a pore size of 0.22 μm to yield 20 ml of a solution of a surfactant-removed solubilized fraction (Ca-LSP-SD) (protein concentration: 1.3 mg/ml).

Example 5

Fractionation of *Candida albicans* Solubilized Fraction (Ca-LSP-S) Using ConA Column The remaining 100 ml of Ca-LSP-S obtained in Example 4 was concentrated by ultrafiltration (protein concentration: 3 mg/ml), and 1.5 times by volume of 20 mM bis-Tris buffer (pH 6.5) was then added to make up a final octylglucoside concentration of 20 mM. To the solution obtained was added NaCl to make up a final concentration of 0.25 M, and further were added $CaCl_2$ and $MnCl_2$ to make up a final concentration of 1 mM. Next, this mixture was then applied to a column of ConA Sepharose 4B (Pharmacia-LKB), previously equilibrated with buffer A (20 mM bis-Tris, 20 mM octylthioglucoside, 0.25 M NaCl, 1 mM $CaCl_2$, 1 mM $MnCl_2$ (pH 6.5)). The non-adsorbed components were washed with buffer A. The effluent fraction and the washed fraction obtained were combined and taken as the ConA column non-adsorbed fraction. Next, the ConA column adsorbed components were then eluted with buffer A containing 0.25 M methyl-D-glucose, and the eluate taken as the ConA column eluted fraction. The ConA column non-adsorbed fraction and the ConA column eluted fraction obtained were concentrated by ultrafiltration (cutoff molecular weight: 10,000), and the concentrates obtained were referred to as "Ca-ConA-Pass" and "Ca-ConA-Elute," respectively.

Example 6

Production of Vaccine Preparations

1) Production of Water-in-Oil (Incomplete Freund's Adjuvant) Preparation

A necessary volume of each of the above-described antigen solutions derived from various LSPs (Ca-LSP etc.), which are insoluble fractions, surfactant-removed solubilized fractions (Ca-LSP-SD etc.) derived from LSP, and ConA column eluted fraction (Ca-ConA-Elute) were taken, and sufficiently mixed with an equal volume of a incomplete Freund's adjuvant (hereinafter referred to as "IFA") (manufactured by Difco) to yield a water-in-oil vaccine preparation.

2) Production of Alum Preparation

A necessary volume of each of the above-described antigen solutions derived from various LSPs, which are insoluble fractions, or surfactant-removed solubilized fractions (Ca-LSP-SD etc.) derived from LSP described above was taken, and an equal volume of alum (manufactured by Pierce) was added dropwise thereto with stirring. After adding the entire content, the mixture was additionally stirred for 30 minutes to yield a vaccine preparation.

Example 7

Comparison of Vaccine Activity of Insoluble Fraction Ca-LSP Derived from *Candida albicans* with HSP and HSS Antigen Solutions and Comparison with Living Cell Vaccine 1) Comparison of vaccine activity of Ca-LSP, HSP and HSS antigen solutions: Each of the Ca-LSP, HSP and HSS antigen solutions obtained in Example 1 was diluted with physiological saline to make up a protein concentration of 400 μg/ml. According to Example 6, an equal volume of IFA was added to each dilution to yield a vaccine preparation, which was then subcutaneously inoculated to C57BL/6 mice (six weeks of age, female, five animals per group) at 0.1 ml per animal to immunize the mice. The group in which physiological saline was given in place of the antigen solution was used for control. One week later, the same volume was again subcutaneously inoculated. Specifically, the dose per animal is 20 μg protein/administration for all antigens. One week after second immunization, all immunized mice were intravenously infected with $2.5 \times 10^5$ cells of *Candida albicans* TIMM 1768 cultured in a Sabouraud dextrose liquid medium. After infection, the mice were observed for survival for 30 days.

The results are shown in Table 1. The insoluble fraction Ca-LSP exhibited more potent vaccine activity than the ribosome fraction (HSP) and the soluble fraction (HSS).

TABLE 1

| Group Administered with | Mean Survival ± SD Days | Number of Surviving Mice after 30 Days/ Number of Mice Used |
|---|---|---|
| Physiological Saline | 5.8 ± 1.6 | 0/5 |
| Ca-LSP | >28.8 ± 2.7 | 4/5 |
| HSP | 7.6 ± 3.4 | 0/5 |
| HSS | 7.4 ± 0.9 | 0/5 |

2) Comparison of vaccine activity of *Candida albicans* insoluble fraction Ca-LSP with living cell vaccine: The concentrations of the Ca-LSP antigen solutions were adjusted to make up a dosage of Ca-LSP of 0.2 μg protein/administration, 2 μg protein/administration, or 20 μg protein/administration. Thereafter, a vaccine preparation was obtained according to Example 6, which was then subcutaneously inoculated to C57BL/6 mice (five animals per group) twice at a one-week interval in the same manner as in item 1) of Example 7 to immunize the mice. In addition, *Candida albicans* TIMM 1768 was subjected to shaking culture overnight in a Sabouraud dextrose medium, and the cells were harvested by centrifugation. The cells were washed with physiological saline, and the cells obtained were suspended in physiological saline to make up a cell density of $1 \times 10^6$ cells/ml, $1 \times 10^7$ cells/ml, or $1 \times 10^8$ cells/ml. To each of suspension was added an equal volume of IFA and mixed, and thereafter subcutaneously inoculated at 0.1 ml per mouse to immunize the mice. One week later, the living *Candida* cells as prepared in the same manner as above were subcutaneously inoculated in the same cell number for each mouse. Specifically, the dosage per mouse is $5 \times 10^4$ cells/administration, $5 \times 10^5$ cells/administration, or $5 \times 10^6$ cells/administration. For control, a mixture of physiological saline and IFA was administered by subcutaneously inoculating twice in a one-week interval. After one week of second immunization, all immunized mice were intravenously infected with $2.5 \times 10^5$ cells of *Candida albicans* TIMM 1768 cultured in a Sabouraud dextrose medium. After infection, the mice were observed for survival for 30 days.

The results are shown in Table 2. Ca-LSP exhibited more potent protective activity against infection even at a dosage of 2 μg protein/administration, and exhibited superior protective activity against infection than the immunity of the living cells.

TABLE 2

| Group Administered with | Dosage at One Time | Mean Survival ± SD Days | Number of Surviving Mice after 30 Days/ Number of Mice Used |
|---|---|---|---|
| Physiological Saline | — | 4.0 ± 1.4 | 0/5 |
| Ca-LSP | 0.2* | 9.6 ± 2.5 | 0/5 |
| | 2 | >27.6 ± 4.3 | 2/5 |
| | 20 | >30.0 ± 0.0 | 5/5 |
| Living Cells | $5 \times 10^4$ | 16.8 ± 6.3 | 0/5 |
| | $5 \times 10^5$ | 19.6 ± 9.0 | 0/5 |
| | $5 \times 10^6$ | >20.8 ± 10.1 | 5/5 |

*μg protein.

Example 8

Protective Activity Against Infection of Surfactant-Removed Solubilized Fraction Derived from *Candida albicans* Insoluble Fraction Ca-LSP After the surfactant-removed solubilized fraction (Ca-LSP-SD) derived from Ca-LSP prepared in Example 4 was diluted to a concentration such that a dose is adjusted to 20 μg protein/administration, a vaccine preparation was produced therefrom according to Example 6. The vaccine preparation was then subcutaneously inoculated to C57BL/6 mice (five animals per group) twice at a one-week interval in the same manner as in item 1) of Example 7 to immunize the mice. For control, a preparation of *Candida albicans* insoluble fraction Ca-LSP with IFA, and a mixture of physiological saline and IFA were administered in the same manner for immunization. One week after immunization, mice were intravenously infected with $2.5 \times 10^5$ cells of *Candida albicans* TIMM 1768. After infection, the mice were observed for survival for 30 days. The results are shown in Table 3. The solubilized fraction LSP exhibited protective activity against infection of the same level as that of the insoluble fraction LSP.

TABLE 3

| Group Administered with | Mean Survival ± SD Days | Number of Surviving Mice after 30 Days/ Number of Mice Used |
|---|---|---|
| Physiological Saline | 6.6 ± 2.9 | 0/5 |
| Ca-LSP | >26.8 ± 4.7 | 2/5 |
| Ca-LSP-SD | >24.6 ± 5.1 | 2/5 |

Example 9

Protective Activity Against Infection of Ca-ConA-Elute Derived from *Candida albicans* Insoluble Fraction Ca-LSP Ca-ConA-Elute obtained in Example 5, the fraction containing high content of a glycoprotein having ConA-binding oligomannose, was diluted with physiological saline to make up a protein concentration of 4 µg/ml. According to Example 6, an equal volume of IFA was added to the dilution to prepare a vaccine preparation, which was then administered to C57BL/6 mice (six weeks of age, female, five animals per group) in the same manner as in item 1) of Example 7 to confirm the protective action against infection with *Candida albicans* TIMM 1768. The results are shown in Table 4. The Ca-ConA-Elute exhibited sufficient protective activity against infection when the dosage is 0.2 µg protein/administration.

TABLE 4

| Group Administered with | Mean Survival ± SD Days | Number of Surviving Mice after 30 Days/ Number of Mice Used |
|---|---|---|
| Physiological Saline | 4.0 ± 1.4 | 0/5 |
| Ca-ConA-Elute | >20.8 ± 12.3 | 2/5 |

Example 10

Vaccine Action of *Candida albicans* Insoluble Fraction Ca-LSP in Various Mouse Candidiasis Systemic Infection Models 1) Protection against infection in vaccinated mice in immunocompetent state: After diluting to a concentration such that a dose of Ca-LSP as prepared in Example 1 is adjusted to 20 µg protein/administration, a vaccine preparation was produced according to Example 6. The vaccine preparation was subcutaneously administered to C57BL/6 mice (five animals per group) twice at a one-week interval to immunize the mice in the same manner as in item 1) of Example 7. For control, a mixture of physiological saline and IFA was administered in the same manner as above for immunization. After second immunization, each immunized mouse was subjected to intraperitoneal administration of 200 mg/kg cyclophosphamide on the third day to give an immunosuppressed state. Four days later, the mice were intravenously infected with $5 \times 10^4$ cells of *Candida albicans* TIMM 1768. After infection, the mice were observed for survival for 30 days. The results are shown in Table 5. Even when the immune response is decreased by cyclophosphamide, the Ca-LSP-immunized group had sufficient protective action against infection.

TABLE 5

| Group Administered with | Mean Survival ± SD Days | Number of Surviving Mice after 30 Days/ Number of Mice Used |
|---|---|---|
| Physiological Saline | 1.6 ± 1.3 | 0/5 |
| Ca-LSP | >27.6 ± 5.4 | 4/5 |

2) Persistence of protection by vaccination with Ca-LSP: After diluting to a concentration such that a dose of Ca-LSP as prepared in Example 1 is adjusted to 20 µg protein/administration, a vaccine preparation was produced according to Example 6. The vaccine preparation was subcutaneously administered to C57BL/6 mice (five animals per group) twice at a one-week interval to immunize the mice in the same manner as in item 1) of Example 7. After second immunization, each mouse was intravenously infected on the thirty-fourth day with $1 \times 10^5$ cells of *Candida albicans* TIMM 1768. After infection, the mice were killed on the twelfth day, and both kidneys were aseptically excised. To the kidneys was added 6 ml of physiological saline, and a homogenate was obtained using a homogenizer. The homogenate was diluted with physiological saline (×1, ×10, ×100). A 100 µl portion of each dilution was spread over a Sabouraud dextrose agar medium and cultured at 30° C. for one day, and the colonies appeared were counted. The results are shown in Table 6. It was evident from the results that immunization with Ca-LSP resulted in a decrease of viable cell numbers in kidneys, with protective immunity against infection lasting even at the thirty-fourth day after immunization.

TABLE 6

| Group Administered with | Colony Forming Units $(\times 10^3)$* |
|---|---|
| Physiological Saline | 9100, 1400, 2800, 1600, —** |
| Ca-LSP | 130, 26, 0, 0, 0 |

*Number of cells forming colonies, in homogenates (6 ml) of both kidneys of each five mice.
**Died before killing.

Example 11

Infection with *Candida albicans* TIMM 0239

After diluting to a concentration such that a dose of Ca-LSP as prepared in Example 1 was adjusted to 20 µg protein/ administration, a vaccine preparation was produced according to Example 6. The vaccine preparation was subcutaneously administered to C57BL/6 mice (five animals per group) twice at a one-week interval in the same manner as in item 1) of Example 7 to immunize the mice. Also, those in which physiological saline was used in place of Ca-LSP were used for control. One week after immunization, each mouse (five animals per group) was intravenously infected with $5 \times 10^5$ or $1 \times 10^6$ cells of *Candida albicans* TIMM 0239, a strain differing from *Candida albicans* TIMM 1768, used for preparation of the immunized antigen. After infection, the mice were observed for survival for 30 days. The results are shown in Table 7. It is evident from the results that when immunized with the LSP derived from a strain of *Candida albicans*, protective immunity against infection to other *Candida albicans* strains is also induced.

TABLE 7

| Count of Infected Cells (Cells) | Group Administered with | Mean Survival ± SD Days | Number of Surviving Mice after 30 Days/ Number of Mice Used |
|---|---|---|---|
| $5 \times 10^5$ | Physiological Saline | 8.6 ± 8.7 | 0/5 |
| $5 \times 10^5$ | Ca-LSP | >30.0 ± 0.0 | 5/5 |

TABLE 7-continued

| Count of Infected Cells (Cells) | Group Administered with | Mean Survival ± SD Days | Number of Surviving Mice after 30 Days/ Number of Mice Used |
|---|---|---|---|
| $1 \times 10^6$ | Physiological Saline | 2.0 ± 0.7 | 0/5 |
| $1 \times 10^6$ | Ca-LSP | >24.0 ± 9.2 | 2/5 |

Example 12

Specific Delayed-Type Hypersensitivity (DTH) Reaction to Ca-LSP of Mice Immunized with Living *Candida albicans* Cells In the same manner as in item 2) of Example 7, C57BL/6 mice (five animals per group) were subcutaneously immunized with $5 \times 10^4$, $5 \times 10^5$, or $5 \times 10^6$ living cells twice at a one-week interval. Also, a Ca-LSP preparation with IFA was subcutaneously administered to C57BL/6 mice (five animals per group) such that doses were adjusted to 0.2, 2, and 20 μg protein/administration twice at a one-week interval to immunize the mice. On the sixth day after immunization, 50 μl of a Ca-LSP antigen solution was subcutaneously administered at a concentration of 200 μg protein/ml to the footpads of each mouse. Twenty-four hours later, footpad swelling was measured.

The results are shown in Table 8. It was evident from these results that the cellular immunity to Ca-LSP was established in individual mice sensitized with living cells in which a DTH reaction for recognizing Ca-LSP as an antigen is induced, i.e., in mice acquiring protective immunity against infection. Also, in the Ca-LSP-immunized mice, potent cellular immunity to Ca-LSP has been induced.

TABLE 8

| Group Administered with | Dosage per Administration | Swelling of Foodpad ± SD ($\times 10^{-2}$ mm) |
|---|---|---|
| Physiological Saline | — | 14.2 ± 9.5 |
| Living Cells | $5 \times 10^4$ cells | 123.0 ± 34.5 |
|  | $5 \times 10^5$ cells | 114.8 ± 21.2 |
|  | $5 \times 10^6$ cells | 144.0 ± 17.1 |
| Ca-LSP | 0.2* | 85.0 ± 16.6 |
|  | 2 | 109.2 ± 26.5 |
|  | 20 | 120.4 ± 18.6 |

*μg protein.

Example 13

Specific Proliferation of Splenic Lymphocytes from Mice Immunized with *Candida albicans* Cells in Response to *Candida albicans* Ca-LSP From BALB/c mice immunized with $5 \times 10^6$ living cells in the same manner as in item 2) of Example 7, spleens were excised on the fifteenth day after final immunization, and homogenized in an RPMI-1640 medium to yield a cell suspension. To this suspension was added an RPMI-1640 medium, and this suspension was washed and centrifuged, after which the cells were re-suspended in an RPMI-1640 medium supplemented with 10% fetal calf serum (FCS). This cell suspension was applied on a nylon wool column and cultured at 37° C. for one hour, followed by elution with the 10% FCS-supplemented RPMI-1640 medium, to yield a T cell-rich fraction. The cells were harvested by centrifugation, and suspended in the 10% FCS supplemented RPMI-1640 medium to make up a cell density of $1 \times 10^7$ cells/ml. After a 100 μl aliquot of an appropriately diluted Ca-LSP antigen solution was poured into each well of a 96-well microplate, the cell suspension was added at 100 μl per well. Two days after cultivation at 37° C. in 5% $CO_2$, $^3$H-thymidine (0.5 μCi/well) was added thereto. After 18 hours of cultivation, the cells were recovered and assayed for the amount of $^3$H-thymidine uptake.

The results are shown in Table 9. The splenocytes derived from immunized mice exhibited dose-dependent proliferation to Ca-LSP.

TABLE 9

| Ca-LSP Concentration** | $^3$H-Thymidine Uptake (cpm) ± SD | Stimulation Index (SI)* |
|---|---|---|
| 0 | 2477 ± 219 | 1.0 |
| 0.05 | 2882 ± 334 | 1.2 |
| 0.5 | 14357 ± 2771 | 5.8 |
| 5 | 41736 ± 2326 | 16.9 |

$$*SI = \frac{[\text{Amount of }^3\text{H-thymidine Uptake with Adding Ca-LSP(cpm)}]}{[\text{Amount of }^3\text{H-thymidine Uptake without Adding Ca-LSP(cpm)}]}$$

**μg protein.

Example 14

Figure 3:
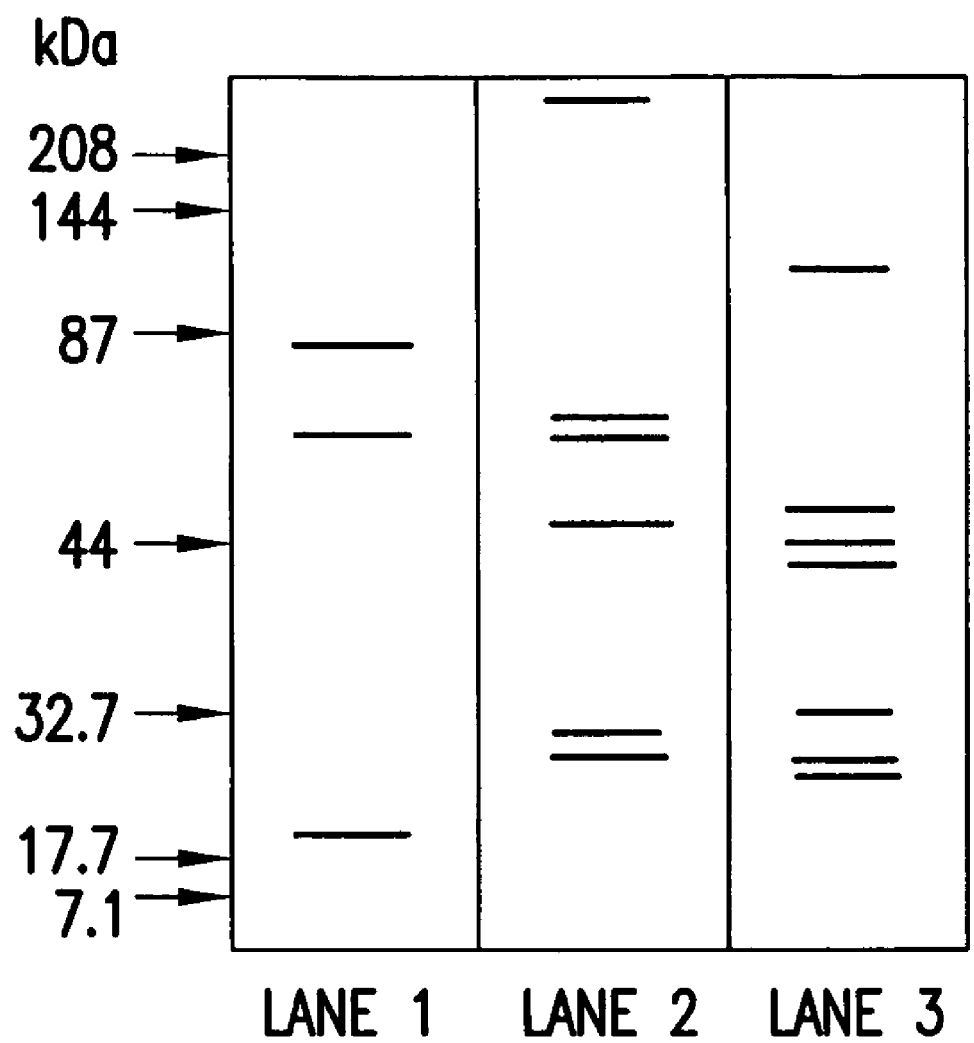
FIG. 3 is a chart showing the presence of antibodies against proteins derived from *Candida albicans* insoluble fraction Ca-LSP contained in mouse anti-*Candida* serum (lane 1), rabbit anti-*Candida* serum (lane 2), and normal individual serum (lane 3).

Antibodies Against Proteins Derived from *Candida albicans* Insoluble Fraction Ca-LSP in Blood from Mammals Immunized or Sensitized with Living *Candida albicans* Cells 1) Antibodies against Ca-LSP-derived proteins in blood from mice immunized with living *Candida albicans* cells: From BALB/c mice immunized with $5 \times 10^6$ living cells in the same manner as in item 2) of Example 7, an anti-*Candida* serum was prepared. Next, a sample buffer for SDS electrophoresis was then added to Ca-LSP, followed by treatment in a boiling water bath for three minutes and subsequently centrifuged. The supernatant was subjected to 12.5% SDS-PAGE. After electrophoresis, the supernatant was blotted onto a PVDF membrane and subjected to blocking overnight with Block Ace. Thereafter, the PVDF membrane was reacted with a 50-fold dilution of the antiserum, and then with a rat anti-mouse IgG antibody as a secondary antibody to detect antigen proteins. As a result, as shown in FIG. 3 (lane 1), IgG antibodies against some proteins contained in Ca-LSP were induced in the serum from immunized mice acquiring protective immunity against infection. The protein of which molecular weight is near 65,000 is the protein described in Example 15.

2) Antibodies against Ca-LSP contained in rabbit anti-*Candida* serum: A commercially available rabbit anti-*Candida* serum (purchased from Dainippon Pharmaceutical) was used as a primary antibody and a goat anti-rabbit IgG antibody as a secondary antibody. The proteins contained in Ca-LSP were separated by SDS-PAGE, blotted onto a PVDF membrane, and subjected to Western blotting to detect an antigenic protein in the same manner as in item 1) of Example 14. As a result, as shown in FIG. 3 (lane 2), antibodies against some of proteins contained in Ca-LSP were contained in the rabbit anti-*Candida* serum. In other words, it was clarified that components of Ca-LSP acted as antigens in the rabbit as well. The protein detected near 65 kD is the same as that described in Example 15.

3) Antibodies against Ca-LSP in human blood: *Candida albicans* is a fungus normally colonizing in humans, and it has been known that almost all humans are sensitized with *Candida albicans* cells. In view of this, in order to evaluate whether or not antibodies against proteins derived from Ca-LSP are present in normal individual blood, proteins derived from Ca-LSP were subjected to Western blotting to detect an antigenic protein in the same manner as in item 1) of Example 14 by using a normal individual serum as a primary antibody and a goat anti-human IgG antibody as a secondary antibody. As shown in FIG. 3 (lane 3), IgG antibodies against some proteins contained in Ca-LSP were detected in the normal individual serum, so that it was clarified that proteins contained in Ca-LSP act as antigens in humans as well.

Example 15

Purification of Antigenic Proteins from *Candida albicans* Solubilized Fraction (Ca-LSP-S) (1)

1) Isolation of proteins: Ca-ConA-Pass as obtained in Example 5 was applied to a MonoQ column (manufactured by Pharmacia-LKB), previously equilibrated with buffer B (20 mM bis-Tris, 20 mM octylthioglucoside, 1 mM $CaCl_2$, 1 mM $MnCl_2$ (pH 6.5)). After column washing with buffer B, elution was carried out on a linear gradient of 0-0.8 M NaCl in buffer B. The fraction obtained was subjected to immunoblotting under the same conditions as in item 1) of Example 14. Fractions containing proteins positive for some of mouse anti-*Candida* sera were collected and dialyzed against buffer B.

The dialyzate obtained was applied to hydroxyapatite (manufactured by Mitsui Toastu Chemicals, Inc.), previously equilibrated with buffer B. After washing with buffer B, elution was carried out on a linear gradient of 0-0.5 M NaCl in buffer B. The fraction eluted was again subjected to immunoblotting under the same conditions as in item 1) of Example 14. A protein having a molecular weight of about 65,000 (SDS-PAGE, under reduced conditions) showing strong binding to the mouse anti-*Candida* serum, and a protein having a molecular weight about 25,000 (SDS-PAGE, under reduced conditions) showing weak binding to the anti-*Candida* serum were isolated.

The N-terminal amino acid sequences of the two proteins obtained were determined by using the L-500 amino acid analyzer (manufactured by Hitachi Ltd.), and it was anticipated that each had amino acid sequences as shown by SEQ ID NO: 1 in Sequence Listing and SEQ ID NO: 2 in Sequence Listing. Based on information obtained, the amino acid sequence was subjected to homology search to known proteins, and it was found that the protein having a molecular weight of about 65,000 (SDS-PAGE, under reduced conditions) had homology with dihydrolipoamide dehydrogenase (DLDH) of *Saccharomyces cerevisiae* localized in mitochondria, and that the protein having a molecular weight of about 25,000 (SDS-PAGE, under reduced conditions) had homology with superoxide dismutase (SOD) of *Saccharomyces cerevisiae* localized in mitochondria, both of which were deduced to be proteins derived from mitochondria.

Separately, the fractions obtained by fractionation of Ca-ConA-Pass through the MonoQ column were assayed for proliferation inductive activity for splenic lymphocytes from immunized mice in the same manner as in Example 13, together with protein separation by SDS-PAGE and analysis by silver staining. The fraction eluted near 0.12 M NaCl from the MonoQ column chromatography of Ca-ConA-Pass was collected, again applied to the MonoQ column, and eluted on a linear density gradient of 0-0.24 M NaCl in buffer B. From the eluted fraction obtained, a protein having a molecular weight of about 30,000 (SDS-PAGE, under reduced conditions) could be isolated.

Similarly, the fraction eluted near 0.64 M NaCl from the MonoQ column was again applied to the MonoQ column chromatography of Ca-ConA-Pass and eluted on a linear density gradient of 0.24-0.8 M NaCl in buffer B. From the eluted fraction obtained, a protein having a molecular weight of about 62,000 (SDS-PAGE, under reduced conditions) could be isolated. These proteins were clearly shown to promote $^3$H-thymidine uptake to splenic lymphocytes of mouse immunized with living fungi prepared in the same manner as in Example 13 at a final protein concentration of 5 µg/ml, demonstrating lymphocyte proliferation inducing activity, though their binding to the mouse anti-*Candida* serum described in item 1) of Example 14 was extremely low.

The N-terminal amino acid sequences of the two proteins obtained were determined by using the L-500 amino acid analyzer (manufactured by Hitachi Ltd.), and it was anticipated that each had amino acid sequences as shown by SEQ ID NO: 3 in Sequence Listing and SEQ ID NO: 4 in Sequence Listing. Based on the information obtained, the amino acid sequence was subjected to homology search to known proteins, and it was found that the protein having a molecular weight of about 30,000 had homology with citrate synthase of *Saccharomyces cerevisiae*, and the protein having a molecular weight of about 62,000 had homology with vacuolar aminopeptidase I of *Saccharomyces cerevisiae*.

2) Antigenicity test for isolated proteins: The four proteins isolated above (the protein having a molecular weight of about 65,000; the protein having a molecular weight of about 25,000; the protein having a molecular weight of about 30,000; and the protein having a molecular weight of about 62,000) were assayed for the amount of $^3$H-thymidine uptake by splenic lymphocytes derived from mice immunized with living fungi in the same manner as in Example 13. As a result, all proteins exhibited lymphocyte proliferation inducing activity at a protein level of 5 µg/ml per assay.

Furthermore, the antigenic proteins described above were subcutaneously administered in the same manner as in Example 12 to the footpads of the mice immunized with living *Candida albicans* cells to test whether or a not a DTH reaction was induced. As a result of the test for the four antigenic proteins described above, all of these proteins gave significant footpad swelling when administered at 5 µg/administration.

It was clarified from the above results that the four proteins isolated were all recognized by individuals acquiring protective immunity against infection.

Example 16

Acquisition of Protective Immunity Against Infection by Transfer of Splenocyte Derived from Mice Immunized with *Candida albicans* Insoluble Fraction Ca-LSP A preparation of Ca-LSP mixed with IFA was subcutaneously administered to BALB/c mice (five animals per group) at 0.1 ml per animal twice at a one-week interval in the same manner as in item 1) of Example 7 to immunize the mice. The dose is 20 µg protein/administration. For control, a mixture of physiological saline and IFA was administered in the same manner as above for immunization. One week after second immunization, spleens were excised from five immunized mice and homogenized in an RPMI-1640 medium to yield a cell suspension (about 8×10⁷ cells/0.5 ml), and the 0.5 ml portion was transferred into C.B.-17/scid mice (five animals per group). One day later, each mouse was intravenously infected with 5×10⁴ cells of *Candida albicans* TIMM 1768. Furthermore, for control, normal (without splenocyte transfer) C.B.-17/scid mice (five animals) were intravenously infected with the same number of cells of *Candida albicans* TIMM 1768. After infection, the mice were killed on the fifth day, and both kidneys were aseptically excised and homogenized with adding 6 ml of physiological saline to yield a homogenate. The resulting homogenate was diluted (×1, ×10, ×100) with physiological saline, and thereafter, a 100 μl portion of each dilution was spread over Sabouraud dextrose agar medium and cultured at 30° C. for one day. The number of the colonies formed were counted. The results were shown in Table 10.

TABLE 10

| Transfer of Splenocytes from Mice | Colony Forming Units (×10²)* | Ave. Colony Forming Units ± SD (×10⁻² cells) |
| --- | --- | --- |
| None (Normal) | 239, 119, 151, 119, 110 | 148 ± 54 |
| Physiological Saline | 21, 61, 85, 155, 172 | 99 ± 64 |
| Ca-LSP | 9, 17, 2, 49, 182 | 52 ± 75 |

*Number of cells forming colonies contained in homogenates (6 ml) of both kidneys of each five mice.

By transferring splenocytes derived from mice immunized with Ca-LSP, the viable cell numbers in kidneys significantly (p<0.05) decreased, as compared with normal mice. In other words, it was clarified that adoptive transfer of immunity with splenocytes of mice immunized with Ca-LSP could be carried out.

Example 17

Vaccine Activity of *Aspergillus fumigatus* Insoluble Fraction Af-LSP

A vaccine preparation, produced according to Example 6 using the Af-LSP antigen solution 1 prepared in item 1) of Example 2, was subcutaneously administered to C57BL/6 mice at 2 or 20 μg protein/administration twice at a one-week interval to immunize the mice. For control, a mixture of physiological saline and IFA was administered in the same manner as above for immunization. After immunization, each mouse was intravenously infected on the eighth day with 2×10⁶ spores of *Aspergillus fumigatus* TIMM 1776. After infection, the mice were observed for survival for 30 days.

The results are shown in Table 11. Prominent protective immunity against infection was observed after two administrations of 20 μg protein/administration, and significant prolongation of survival days could be seen even at 2 μg protein/administration. In other words, it was also shown that Af-LSP could be used as a vaccine.

TABLE 11

| Group Administered with | Dosage per Administration | Mean Survival ± SD Days | Number of Surviving Mice after 30 Days/ Number of Mice Used |
| --- | --- | --- | --- |
| Physiological Saline | — | 5.3 ± 0.5 | 0/6 |
| Af-LSP | 2* | 9.6 ± 4.8 | 0/5 |
|  | 20 | >11.7 ± 6.5 | 2/6 |

*μg protein.

Example 18

Antibodies Against Proteins Derived from *Aspergillus fumigatus* Insoluble Fraction Af-LSP in Blood from Mice Administered with Living *Aspergillus fumigatus* Cells A suspension of *Aspergillus fumigatus* TIMM 1776 spores (1×10⁸ spores/ml) was mixed with an equal volume of complete Freund's adjuvant, and 0.1 ml of the resulting mixture was subcutaneously administered to BALB/c mice twice at a one-week interval to immunize the mice. One week after immunization, blood was collected to obtain an anti-*Aspergillus* serum.

Figure 4:
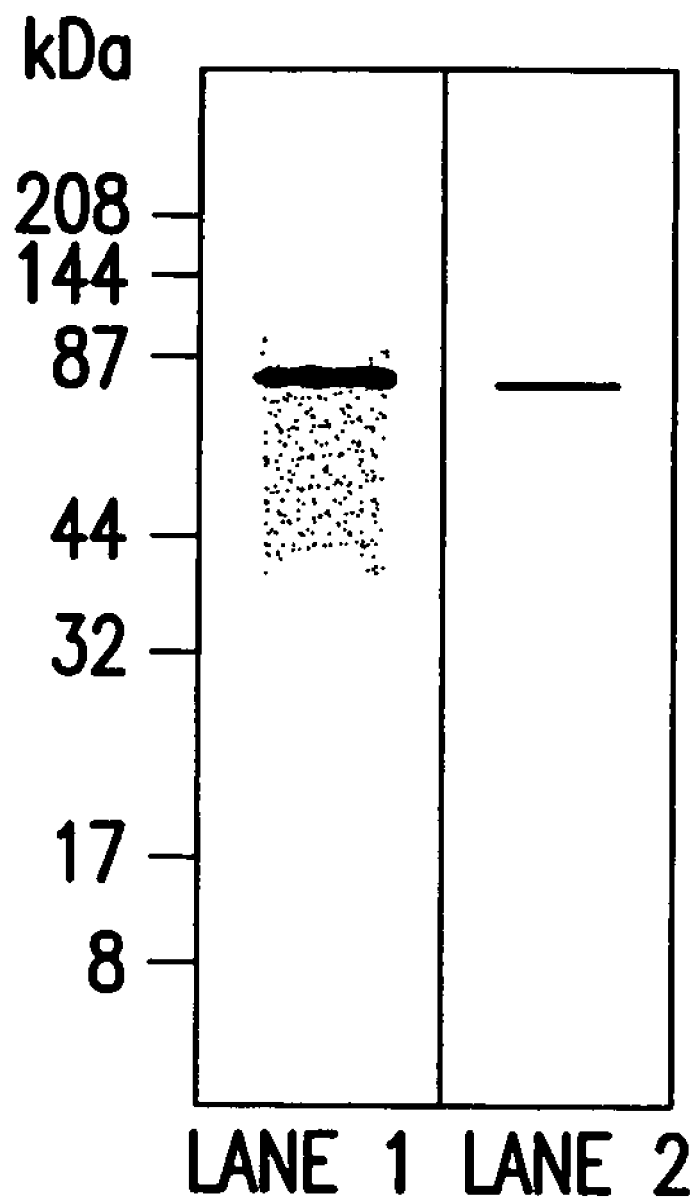
FIG. 4 is a chart showing the presence of antibodies against a protein derived from *Aspergillus fumigatus* insoluble fraction Af-LSP (lane 1), and a protein derived from the *Cryptococcus neoformans* insoluble fraction Crn-LSP (lane 2), each being contained in mouse anti-*Aspergillus* serum.

After the Af-LSP antigen solution 1 prepared in item 1) of Example 2 was separated by SDS-PAGE, the separated components were blotted onto a PVDF membrane to detect antigenic proteins by Western blotting in the same manner as in item 1) of Example 14 using the anti-*Aspergillus* serum as a primary antibody and a rabbit anti-mouse IgG antibody as a secondary antibody. As a result, as shown in FIG. 4 (lane 1), antibodies against proteins in Af-LSP were contained. In other words, the proteins contained in Af-LSP are recognized as antigens by the living body suffering from *Aspergillus* infection. Therefore, as described in Example 17, it appears that specific protective immunity can be performed by inducing immunity to Af-LSP.

Example 19

Cross Reactivity Among Insoluble Fractions Derived from Fungi)

Figure 5:
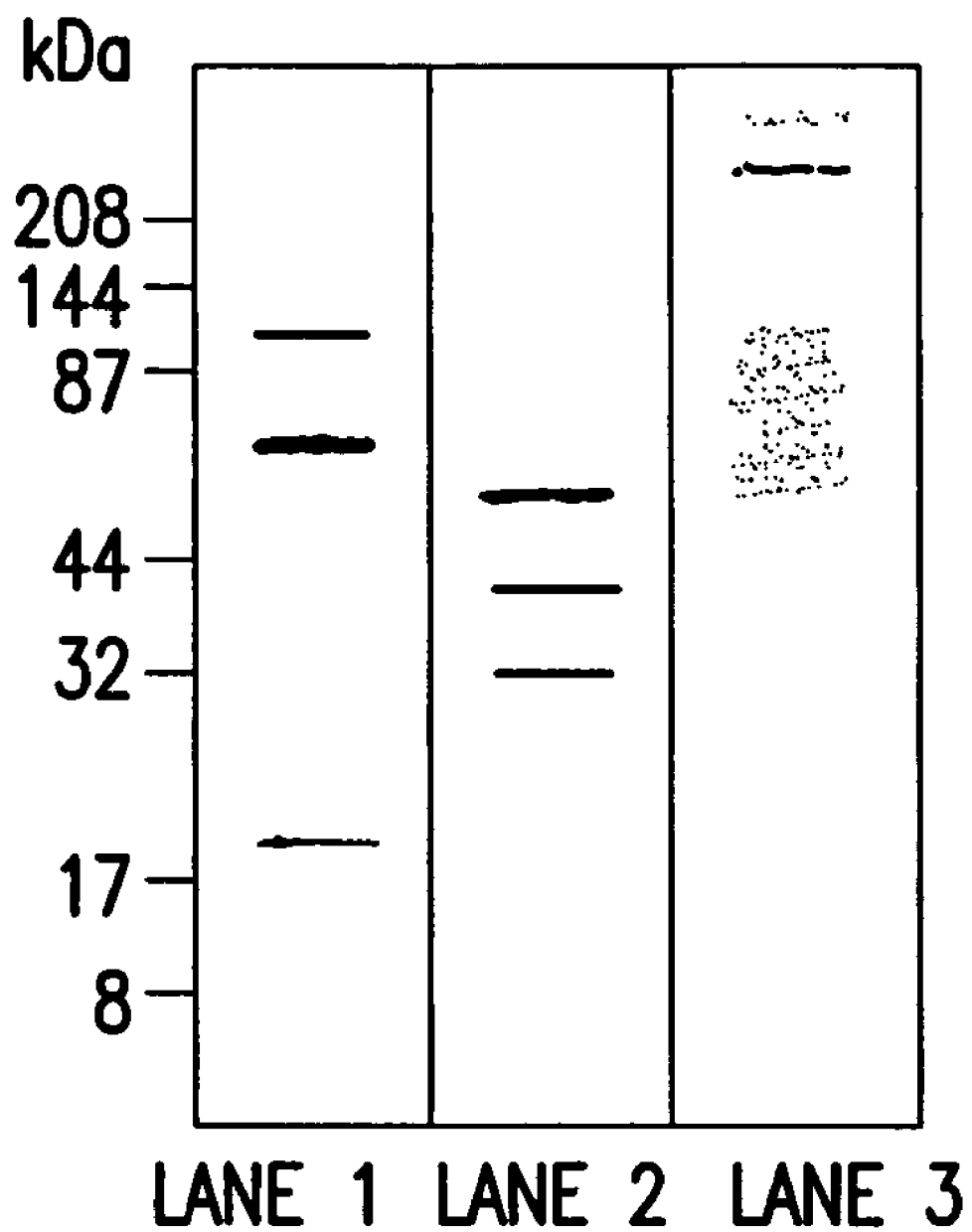
FIG. 5 is a chart showing the presence of antibodies against a protein derived from *Candida albicans* insoluble fraction Ca-LSP (lane 1), a protein derived from the *Cryptococcus neoformans* insoluble fraction Crn-LSP (lane 2), and a protein derived from the *Aspergillus fumigatus* insoluble fraction Af-LSP (lane 3), each being contained in mouse anti-*Candida* serum.

1) Cross reactivity of anti-*Candida* serum or anti-*Aspergillus* serum to proteins derived from other kinds of fungi: Af-LSP antigen solution 1 and Crn-LSP were separated by SDS-PAGE, and each was blotted onto a PVDF membrane to detect antigenic proteins by Western blotting in the same manner as in item 1) of Example 14 using an anti-*Candida* serum [item 1) of Example 14] as a primary antibody and a rabbit anti-mouse IgG antibody as a secondary antibody. As a result, as shown in FIG. 5, the anti-*Candida* serum exhibited cross reactivity to proteins derived from Crn-LSP (lane 2). Also observed was weak cross reactivity to Af-LSP derived from *Aspergillus* (lane 3). Incidentally, lane 1 shows an example where an insoluble fraction, Ca-LSP, was used.

Also, after separation of Crn-LSP by SDS-PAGE, the separated components were blotted onto a PVDF membrane to detect antigenic proteins by Western blotting in the same manner as in item 1) of Example 14 using an anti-*Aspergillus* serum (Example 18) as a primary antibody and a rabbit anti-mouse IgG antibody as a secondary antibody. The anti-*Aspergillus* serum exhibited weak but detectable cross reactivity to a protein contained in Crn-LSP derived from *Cryptococcus* (FIG. 4, lane 2).

2) Induction of specific cellular immunity and cellular immunity against Af-LSP in Ca-LSP-immunized mice: A preparation of Ca-LSP mixed with IFA and a preparation of Af-LSP antigen solution No. 1 mixed with IFA were subcutaneously administered to C57BL/6 mice twice at a one-week interval at 0.2 µg protein/administration, 2 µg protein/administration, or 20 µg protein/administration to immunize the mice. For control, immunization was carried out with a mixture of physiological saline and IFA in the same manner as above. After immunization, Af-LSP was subcutaneously administered on the sixth day to the footpads of each mouse (five animals per group) at 20 µg protein/50 µl. Twenty-four hours later, the footpad swelling was measured. The results are shown in Table 12. From the finding that the swelling was greater in the Af-LSP-immunized group, it was clarified that a DTH reaction with considerable selectivity to Af-LSP was induced. On the other hand, a significant DTH reaction to Af-LSP occurred in the group immunized with Ca-LSP at 20 µg protein, which clarified that the cellular immunity involving a cross reaction was induced. In other words, the presence of a protein showing a cross reaction with different fungi was demonstrated. Therefore, it appears that infection with different fungi by the use of a single kind of LSP can be protected (see Example 20).

TABLE 12

| Group Administered with | Dosage per Administration | Swelling of Foodpad ± SD ($\times 10^{-2}$ mm) |
|---|---|---|
| Physiological Saline | — | 6.8 ± 5.8 |
| Af-LSP | 0.2* | 21.0 ± 16.1 |
|  | 2 | 42.6 ± 18.8 |
|  | 20 | 90.0 ± 37.1 |
| Ca-LSP | 0.2* | 7.4 ± 3.4 |
|  | 2 | 5.2 ± 5.7 |
|  | 20 | 28.0 ± 10.9 |

*µg protein.

Example 20

Vaccine Activity of *Candida albicans* Insoluble Fraction Ca-LSP in Mouse Aspergillosis Infection Model A preparation of Ca-LSP mixed with IFA was subcutaneously administered to C57BL/6 mice twice at a one-week interval at 20 µg protein/administration to immunize the mice. For control, immunization was carried out with a mixture of physiological saline and IFA in the same manner as above. After immunization, mice were intravenously infected on the eighth day with $2\times10^6$ spores of *Aspergillus fumigatus* TIMM 1776. After infection, the mice were observed for survival for 30 days. The results are shown in Table 13. It was demonstrated that protective immunity against infection to *Aspergillus* infection can be induced by immunizing with Ca-LSP.

TABLE 13

| Group Administered with | Mean Survival ± SD Days | Number of Surviving Mice after 30 Days/ Number of Mice Used |
|---|---|---|
| Physiological Saline | 6.4 ± 0.9 | 0/6 |
| Ca-LSP | >22.6 ± 9.0 | 2/5 |

Example 21

Preparation of *Candida albicans* Mycelial Cells and Preparation of Insoluble Fraction Ca-LSP-M Derived from Mycelical Cells In the same manner as in Example 1, a portion of a culture obtained by subjecting *Candida albicans* TIMM 1768 to shaking culture in the YPD medium at 30° C. for 24 hours was inoculated to an RPMI-1640 medium supplemented with 10% FCS in an Erlenmeyer flask, and subjected to shaking culture at 37° C. for four hours, to yield *Candida albicans* mycelial cells. The culture was filtered with a glass filter, and after recovery, the cells were washed with the SSB solution, and then re-suspended in the SSB solution. The suspension was then treated with ZYMOLYASE, a *Trichoderma* lysing enzyme in the same manner as in Example 1. In order to separate mycelial cells with protoplast cells, the suspension was filtered by a glass filter, and the filtrate was recovered. The filtrate obtained was centrifuged at 1,000×g for 5 minutes to harvest protoplast cells. These cells were washed with the SSB solution, after which sterile physiological saline was added. After being sufficiently stirred, the mixture was allowed to stand on ice for 10 minutes. After having confirmed of bursting of the protoplast cells, the mixture was centrifuged at 10,000×g for 30 minutes, and the precipitate obtained was taken as the insoluble fraction derived from mycelial cells (hereinafter referred to as "Ca-LSP-M").

Figure 6:
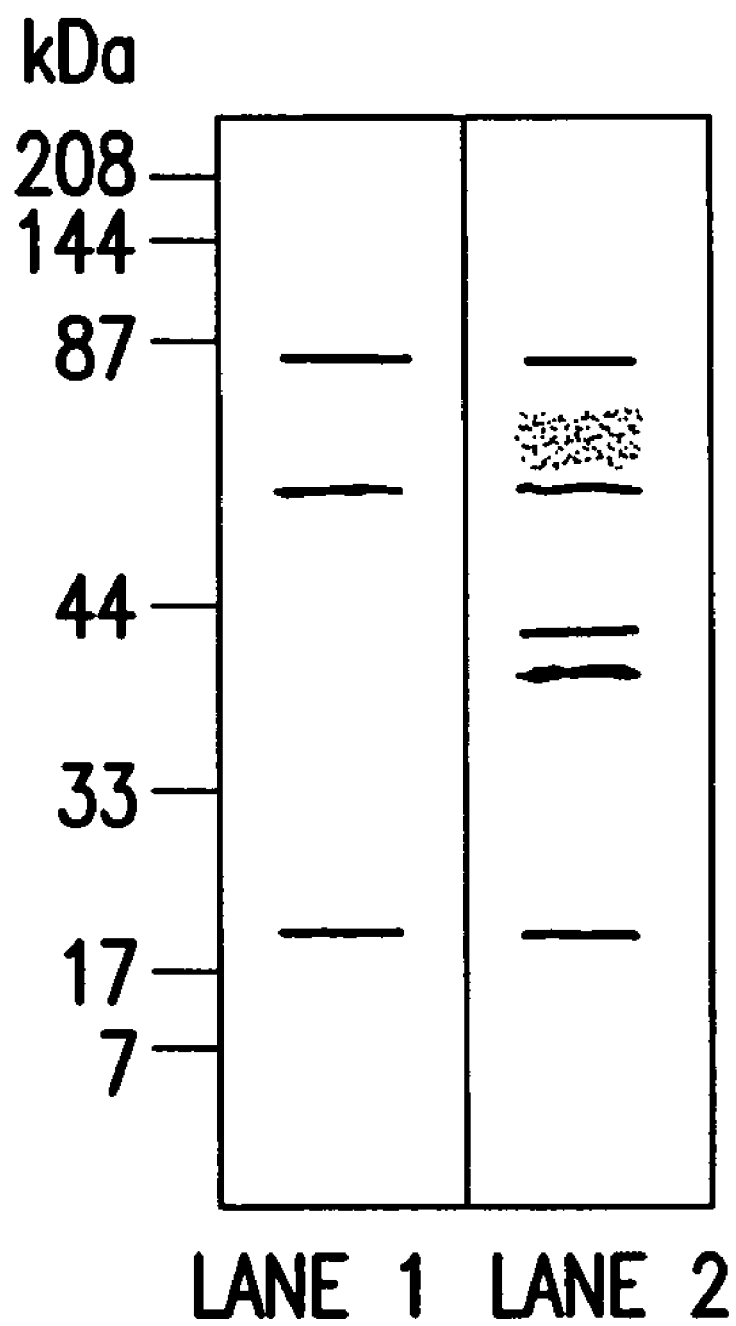
FIG. 6 is a chart showing the presence of antibodies against a protein derived from yeast type *Candida albicans* insoluble fraction Ca-LSP (lane 1), and a protein derived from the mycelial *Candida albicans* insoluble fraction Ca-LSP-M (lane 2), each being contained in mouse anti-*Candida* serum.
Figure 7A:
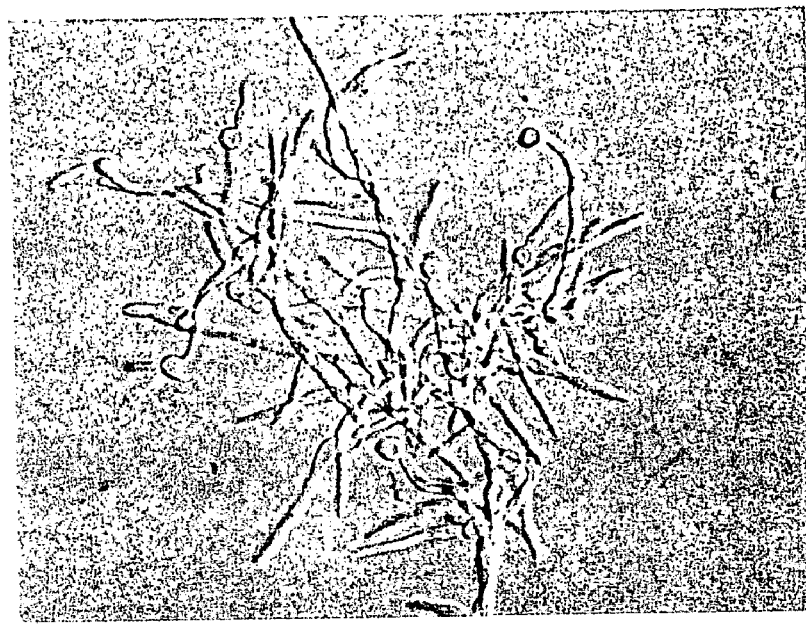
FIG. 7 is figures showing morphologies beforehand after cell wall removal from mycelial *Candida albicans* cells, the figures being taken at a magnification of ×400 using a differential interference microscope (manufactured by NIKON Corporation), wherein A shows cells before cell wall removal, and B shows cells after cell wall removal.
Figure 7B:
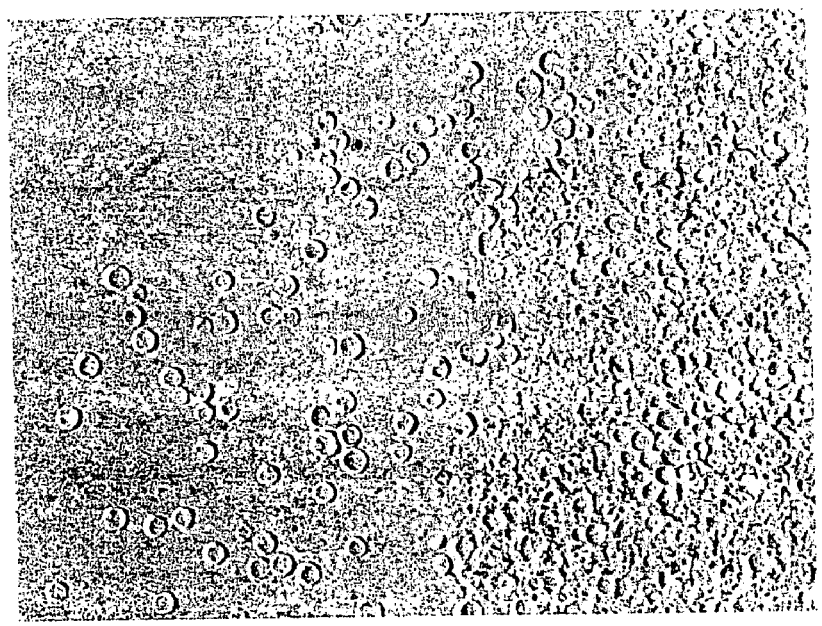

After suspending in physiological saline, Ca-LSP-M was subjected to ultrasonic treatment, and then sterilized in a boiling water bath for 5 minutes, to yield 2 ml of a Ca-LSP-M antigen solution containing membrane proteins etc. (protein concentration: 1.2 mg/ml) from 100 ml of the cell culture. After Ca-LSP-M and control Ca-LSP (both containing about 4 µg of protein) were separated by SDS-PAGE, each was blotted onto a PVDF membrane to detect antigenic proteins by Western blotting in the same manner as in item 1) of Example 14 using an anti-*Candida* serum [item 1) of Example 14] as a primary antibody and a rat anti-mouse IgG antibody as a secondary antibody. As a result, as shown in FIG. 6 (lane 2), IgG antibodies induced against some proteins contained in Ca-LSP-M were detected in the anti-*Candida* serum, with bands distinguishable from that of Ca-LSP of yeast phase cells on lane 1 of FIG. 3 (FIG. 6, lane 1). In addition, the amount of antibodies appeared to be greater. The morphological changes in the *Candida albicans* mycelial cells used in this Example before and after cell wall removal treatment are shown in FIG. 7.

Example 22

Diagnosis by Human Skin Test

The physiological saline solution of Ca-LSP obtained in Example 1 (protein concentration: 2.3 mg/ml) was diluted with physiological saline to make up a protein concentration of 1.0 mg/ml, after which it was further diluted 100-folds and 1,000 folds. The skin test was performed as follows. Patch Star (manufactured by Torii Pharmaceutical Co., Ltd.), previously impregnated with 20 µl of each dilution, was attached on the arm skin of four volunteers for two days, and then the Patch Star was removed. The skin reaction for erythema and papules was observed one hour later. The judgment was made according to the criteria of the International Contact Dermatitis Research Group (ICDRG). Of the four volunteers, two with allergic predisposition showed clear erythema, and one showed slight erythema. Accordingly, the fungal antigen of the present invention was shown to be effective in the diagnosis utilizing the DTH reactions in individuals.

Example 23

Determination of IqE Antibody Titer in Human Plasma

Paper discs were activated with cyanogen bromide, and the antigen (a solution prepared by diluting Ca-LSP-S obtained in Example 4 to make up 100 μg/ml protein concentration) was coupled to the paper discs according to the method of Miyamoto et al. [Miyamoto et al., *Allergy*, Vol. 22, 584-594 (1973)]. The IgE antibody titer in human plasma was determined as described below. One paper disc coupled with the antigen as prepared above and 50 μl of human serum were added to a polystyrene tube, and allowed to stand at room temperature for three hours. Next, the paper disc was washed three times with physiological saline containing 0.2% Tween 20, after which 50 μl of $^{125}$I-labeled anti-human IgE antibody in the RAST-RIA kit (manufactured by Pharmacia) was added, and the plate was kept standing at room temperature for 16 hours.

After the disc was further washed three times with the above washing solution, radioactivity was determined using a gamma counter. At the same time, the IgE antibody titer was calculated from a standard curve prepared with a control reagent of the RAST-RIA kit. Of the allergic patients, twenty-four positive patients for skin test with a commercially available diagnostic intracutaneous allergen extract (manufactured by Torii Pharmaceutical Co., Ltd.) were subjected to measurement for IgE antibody titration against Ca-LSP-S, and as a result, 15 showed positive responses (positive being defined as 0.35 PRU/ml or higher). Therefore, the positive rate to Ca-LSP-S was high in allergic patients, which clarified that the fungal antigen of the present invention consisting of an insoluble fraction is effective in the detection of IgE antibodies.

Example 24

Cytokine Production from Human Peripheral Blood Mononucleated Cells (PBMCs) by Ca-LSP PBMCs were obtained by leukopheresis from normal individuals, followed by collecting the leukocyte fraction, and further separation processes described below. Specifically, the fraction was about 2-fold diluted with an RPMI-1640 medium, then overlayered on a centrifugation separation medium of Ficoll-Paque (manufactured by Pharmacia) and centrifuged at 500×g and room temperature for 20 minutes. The intermediary PBMC layer was recovered by pipetting, washed, and suspended in a solution consisting of 90% fetal bovine serum (FCS, manufactured by Intergen) and 10% dimethyl sulfoxide (manufactured by Sigma) for preservations in liquid nitrogen. The treatment of PBMC with Ca-LSP was carried out as described below.

After being lysed, the above PBMC sample in storage was suspended in an RPMI-1640 medium supplemented with human AB serum (manufactured by Irvine Scientific) to make up a final concentration of 5% (v/v). This suspension was diluted to a cell density of $1.5 \times 10^6$ cells/ml and dispensed into wells of a 24-well microplate at 1 ml per well. Next, a Ca-LSP antigen solution, prepared by diluting the solution of Ca-LSP in physiological saline obtained in Example 1 (protein concentration: 2.3 mg/ml) was added at 50 μl/well to be 5 μg protein/well, followed by cultivation at 37° C. in 5% $CO_2$. On the seventh day after cultivation initiation, the culture supernatant was collected and assayed for IFN-γ content using a human IFN-γ ELISA kit (manufactured by Amersham LIFE SCIENCE). This measurement was carried out according to the protocol of the manufacturer. Here, the detection limit of the kit is 0.002 ng/ml.

Figure 8:
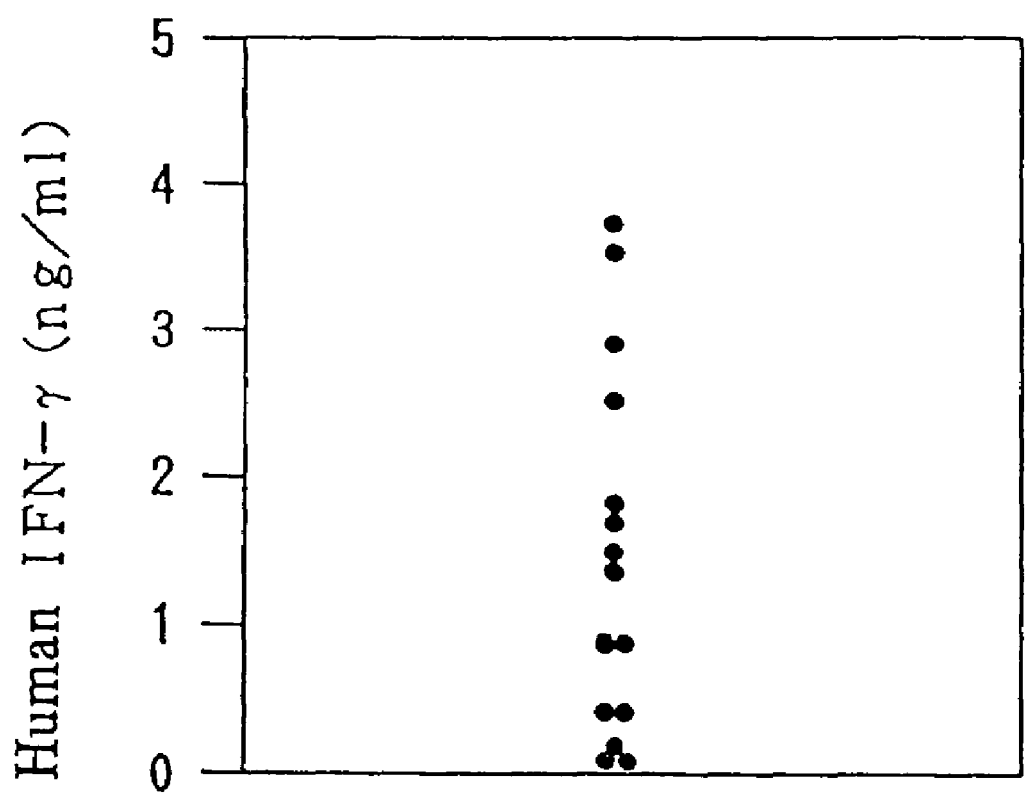
FIG. 8 is a graph showing the amount of human IFN-γ produced after 7 days from initiation of cultivation in an RPMI-1640 medium containing human peripheral blood mononucleated cells (PBMCs) supplemented with the Ca-LSP antigen liquid.
Figure 9:
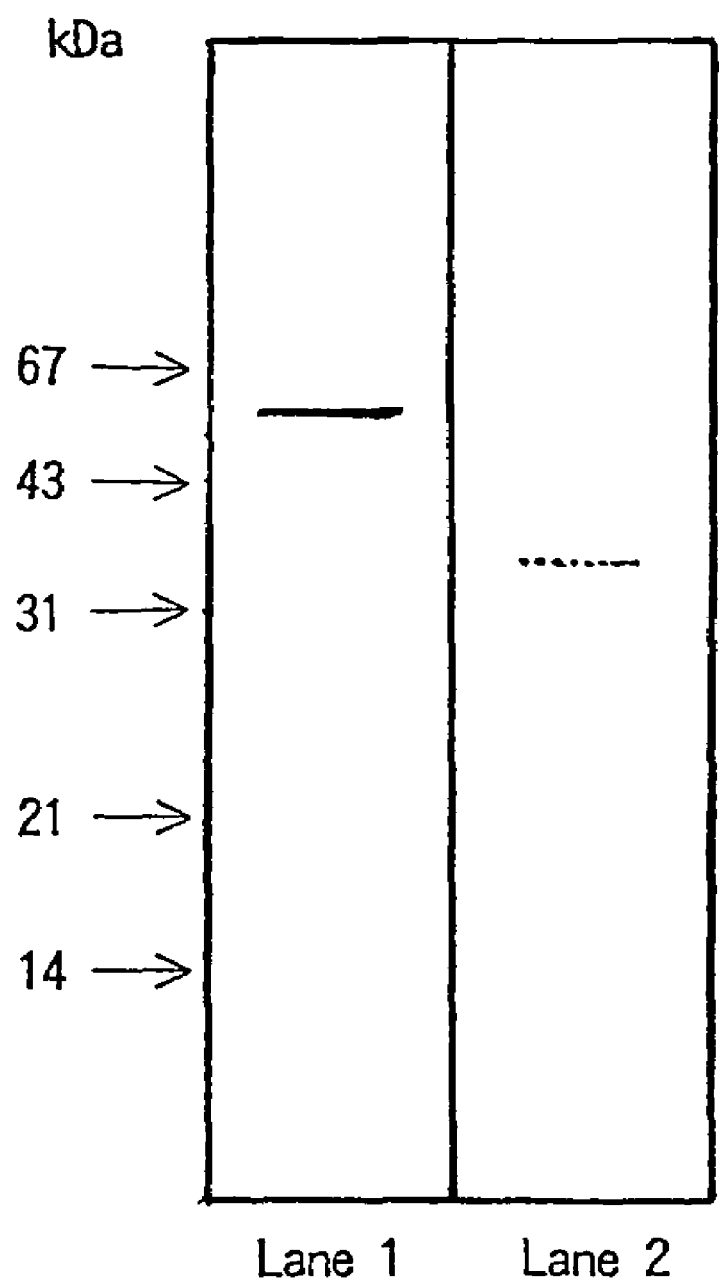
FIG. 9 is a chart showing the presence of antibodies against an antigenic protein derived from *Candida albicans* insoluble fraction Ca-LSP (lane 1, lane 2) contained in mouse anti-*Candida* serum.

The IFN-γ contents on the seventh day are shown in FIG. 8. Human PBMCs produced IFN-γ in response to Ca-LSP. Incidentally, the amount of IFN-γ produced in the 15 samples was in the range 1.435±1.210 (mean±SD) ng/ml.

For control, physiological saline at 50 μl/well was added in place of the Ca-LSP antigen solution, and IFN-γ contents were determined in the same manner as above. The amount of IFN-γ detected in these wells was not more than the detection limit of the kit.

Example 25

Preparation of Reagent for Intradermal Test and Titration Reagent for Diagnosis of Fungal Allergy A Ca-LSP antigen solution prepared in Example 1 is dried and collected as a powder to be used as a reagent for intradermal test to fungal allergy and as a titration reagent for the diagnosis of the fungal allergy. The reagent for intradermal test is prepared by 1,000-fold dilution to make up a 1 mg/ml protein concentration using as a solvent a 0.9% physiological saline supplemented with 0.5% phenol. The titration reagent for the diagnosis of the fungal allergy is prepared by using the dilution of a stock solution as a titration reagent for histamine release, which is dissolved in Hank's buffer in a 1 mg/ml protein concentration.

Example 26

Preparation of Antigenic Agent for Desensitization Therapy

A Ca-LSP antigen solution prepared in Example 1 is dried and collected as a powder to be used as a therapeutic agent for desensitization to fungal allergen. The active component as allergen is dissolved in a 0.9% physiological saline supplemented with 0.5% phenol at a concentration of 1 mg/ml to give a stock solution of an antigen for desensitization therapy.

Example 27

Isolation of Nucleic Acid Encoding *Candida albicans* Antigenic Protein

1) Isolation of DNA encoding a protein having a molecular weight of about 65,000: In order to isolate a nucleic acid encoding a protein having a molecular weight of about 65,000 (hereinafter referred to as 65k protein) which was isolated in item 1) of Example 15, firstly, a cDNA library for *Candida albicans* TIMM 1768 was prepared.

In order to extract and purify a total RNA from fungal cells, the above fungi were first cultured in 200 ml of the YPD medium at 35° C. Thereafter, the resulting cells were recovered by centrifugation at 2000×g for 5 minutes, and then washed once with distilled water. The obtained cells were rapidly frozen by liquid nitrogen. Thereafter, the frozen cells were disrupted to a powdery state with a mortar. A total RNA was recovered and isolated from the resulting disrupted cells by using RNA extraction kit manufactured by Pharmacia. poly(A)$^+$ RNA was prepared from the above total RNA by using Oligotex-dT 30<Super> (manufactured by Takara Shuzo Co., Ltd.). Next, cDNA was prepared from 5 μg of the poly(A)+ RNA by using Takara cDNA synthesis kit (manufactured by Takara Shuzo Co., Ltd.). After ligation of the synthesized cDNA with a lambda phage vector λSCREEN-1 (manufactured by Novagen), a cDNA library was constructed by carrying out in vitro packaging by phage maker system, Phage Pack Extract (manufactured by Novagen).

It was deduced that the 65k protein is DLDH homolog from *Saccharomyces cervisiae* based on the analysis for amino acid sequence in item 1) of Example 15. An oligonucleotide DL2 having a nucleotide sequence complementary to the nucleotide sequence which was deduced to encode an amino acid sequence, a highly conserved amino acid sequence in DLDHs from other organisms, and an oligonucleotide having a nucleotide sequence which was deduced to encode a partial sequence of the amino acid sequence of SEQ ID NO: 1 in Sequence Listing was synthesized and purified to be used as primers for PCR. The nucleotide sequence for DL1 is shown by SEQ ID NO: 9 in Sequence Listing, and the nucleotide sequence for DL2 is shown by SEQ ID NO: 10 in Sequence Listing. Genomic DNA was extracted and purified from *Candida albicans* TIMM1768 by the method of P. Philippsen et al [*Methods in Enzymology*, 194, 169-175 (1991)], in order to use it as a template for PCR. PCR was carried out using the purified genomic DNA as a template and DL1 and DL2 as primers. The reaction conditions for PCR were 30 cycles of temperature shifts consisting of 94° C. for 1 minute, 55° C. for 1.5 minutes, and 72° C. for 2 minutes. As a result, a DNA having a length of about 1 kbp was amplified. After cloning of the above DNA into pUC118 vector (manufactured by Takara Shuzo Co., Ltd.), its nucleotide sequence was determined. The nucleotide sequence of the amplified DNA was as shown by SEQ ID NO: 13 in Sequence Listing. In addition, the amino acid sequence deduced to be encoded by the above nucleotide sequence had an amino acid sequence identical to that of the determined N-terminal of the 65k protein. Therefore, it was obvious that the amplified DNA fragment obtained was a partial portion of a DNA encoding the 65k protein.

Next, in order to obtain the whole cDNA encoding the 65k protein, screening of the cDNA library was carried out using the above amplified DNA fragment as a probe. The cDNA library obtained as described above was inoculated to a host *Escherichia coli* ER1647, mixed with top agarose (LB medium containing 0.7% agarose), and the mixture was overlayed on an LB plate, and then cultured at 37° C. overnight to form plaques. The resulting plaques were transferred to nylon membrane (Hybond-N, manufactured by Amersham), and thereafter, plaque hybridization was carried out. The above PCR fragment with 1 kb was labelled by a random primer DNA labelling kit (manufactured by Takara Shuzo Co, Ltd.) and [α-$^{32}$P] dCTP and used as the probe for hybridization. As a result of screening of 1.6×10$^5$ plaques, a large number of phage clones hybridized with the probe. Twenty-eight clones out of the hybridized clones which exhibited strong signals were further analyzed. Automatic subcloning in *Escherichia Coli* gave *Escherichia coli* clones harboring plasmids which resulted from automatic subcloning of a region containing cDNAs from these phages. Plasmids were purified from the above *Escherichia coli*, and then the length of cDNAs and patterns for DNA bands resulting from restriction endonuclease digestion of the cDNAs were evaluated. Thereafter, a cDNA which is considered to contain the 65k protein gene was selected, and then the nucleotide sequence thereof was determined. The DNA nucleotide sequence was shown by SEQ ID NO: 7. It was deduced that the 65k protein was the protein having the amino acid sequence as shown by SEQ ID NO: 5 in Sequence Listing.

2) Isolation of DNA encoding an antigenic protein having a molecular weight of about 25,000: In order to isolate a DNA encoding a protein having a molecular weight of about 25,000 (hereinafter, referred to 25K protein) which was isolated in item 1) of Example 15, firstly, oligonucleotides SO1 and SO2 which were respectively deduced to encode partial portions of the amino acid sequence of SEQ ID NO: 2 in Sequence Listing were synthesized, purified, and used as primers for PCR. The nucleotide sequence of SO1 is shown by SEQ ID NO: 11 in Sequence Listing, and the nucleotide sequence of SO2 is shown by SEQ ID NO: 12 in Sequence Listing. Next, RT-PCR was carried out using Takara RNA LA PCR kit (AMV) Ver. 1.1 (manufactured by Takara Shuzo Co., Ltd.) by the use of 0.5 μg of the isolated poly(A)+ RNA. Specifically, cDNA was synthesized from 0.5 μg of poly(A)+ RNA by a reaction of AMV reverse transcriptase (at 45° C., for 30 minutes) using oligo(dT)20-M4 adaptor primer. PCR was carried out using the above cDNA as a template and SO1 primer and M13M4 primer (manufactured by Takara Shuzo Co., Ltd.) as primers under condition of 35 cycles of temperature shifts consisting of 94° C. for 0.5 minute, 55° C. for 2 minutes, and 72° C. for 2 minutes. A second PCR (nested PCR) was also carried out using the resulting reaction mixture for PCR as a template. SO2 primer and M13M4 primer were used as primers in this reaction. As a result of PCR, a DNA with a length of about 700 bp was amplified. After cloning of the above amplified DNA to pUC118 vector, a nucleotide sequence was determined. The determined nucleotide sequence is shown by SEQ ID NO: 8 in Sequence Listing. The amino acid sequence which is deduced to be encoded by the above nucleotide sequence is shown by SEQ ID NO: 6 in Sequence Listing. N-terminal portion thereof was identical to the amino acid sequence determined from the 25k protein. It was clear that the PCR fragment was a DNA encoding the 25k protein having homology with SOD.

Example 28

Purification of Antigenic Proteins from *Candida albicans* Solubilized Fraction (Ca-LSP-S) (2)

Another cultivated *Candida albicans* cells were used to prepare Ca-ConA-Pass in the same manner as in Example 5. The resulting concentrate was purified in the same manner as in Example 15 to search for a novel antigenic protein. As a result, novel proteins having a molecular weight of about 55,000 (SDS-PAGE, under reduced conditions) showing strong binding to the mouse anti-*Candida* serum, and having a molecular weight about 35,000 (SDS-PAGE, under reduced conditions) showing weak binding to the anti-*Candida* serum were isolated. The protein having a molecular weight of about 55,000 had the partial amino acid sequence as shown by SEQ ID NO: 15. The protein having a molecular weight of about 55,000 was identified as catalase from the findings that this partial amino acid sequence had an identical sequence with a partial amino acid sequence of 2nd to 31st residues starting from the N-terminal of the protein encoding a catalase gene CAT1 of *Candida albicans*, and that both proteins had no contradictions in terms of their molecular weights. The protein having a molecular weight about 35,000 had the partial amino acid sequence as shown by SEQ ID NO: 14, and this sequence had homology with malate dehydrogenase of *Saccharomyces cerevisiae*.

Example 29

Production of Antigen Preparation for Nasal Administration

Equal volumes of an aqueous solution of cholera toxin B subunit, prepared to make up a concentration of 1 mg/ml of cholera toxin B subunit (manufactured by Sigma) in distilled water for injection (manufactured by Otsuka Pharmaceutical Co., Ltd.), and the antigen solution Ca-LSP (protein concentration: 1 mg/ml) obtained in Example 1 were mixed to prepare an antigen preparation for nasal administration.

Example 30

Protection Against Infection with Antigen Preparation for Nasal Administration

The antigen preparation produced in Example 29 was nasally administered in 20 μl portions to each of C57BL/6 mice under anethesia. After 1, 3 and 5 weeks after administration, the same volume of the antigen preparation was again nasally administered to the mice. This was referred to "group immunized with Ca-LSP." Incidentally, as a control, each of the preparations obtained by using a physiological saline solution of ovalbumin prepared to make up a concentration of 1 mg/ml, or a physiological saline, in place of the Ca-LSP used in Example 29 was similarly administered, and each was referred to "group immunized with ovalbumin" or "group immunized with physiological saline." On the eighth day after the final preparation administration, blood was drawn from each group of mice, and the anti Ca-LSP antibody titer in sera was measured. As a result, an increase of the antibody titer was observed in the mice of the group immunized with Ca-LSP. In addition, on the sixteenth day after the final preparation administration, a Ca-LSP antigen solution was subcutaneously administered at a concentration of 10 μg protein/50 μl to the footpads of each group of mice. Twenty-four hours later, footpad swelling was measured. As a result, prominent DTH reaction was observed in the group of mice immunized with Ca-LSP.

On the tenth day from the final preparation administration, the mice in each group were intravenously inoculated with 0.5 ml of a cell suspension of *Candida albicans* TIMM 0136 ($2\times10^5$ cells/ml). One week after the cell administration, the mice were killed, and both kidneys were aseptically excised and homogenized with adding 6 ml of physiological saline to yield a homogenate. The resulting homogenate was diluted twice or twenty times with physiological saline, and thereafter, a 100 μl portion of each dilution was spread over Sabouraud dextrose agar plate medium and cultured at 30° C. for two days. The number of the colonies formed were counted. The results were shown in Table 14.

TABLE 14

| Group Administered with | Ave. Colony Forming Units ± SD ($\log_{10}$) |
|---|---|
| Ovalbumin | 4.14 ± 0.61 |
| Ca-LSP | 2.85 ± 0.79 |
| Physiological Saline | 4.00 ± 0.44 |

It was found that the cell numbers in kidneys significantly decreased in group administered with Ca-LSP.

It was clarified from the above results that mice administered with the preparation produced in Example 29 acquired protective immunity against infection to *Candida albicans*.

Example 31

Preparation of *Candida* Antigen

To 100 ml of the Ca-LSP antigen solution obtained in Example 1 at a concentration of 2.3 mg protein/ml was added 25 ml of a 5% aqueous sodium lauryl sulfate (SDS) solution. After stirring the liquid mixture at 4° C. overnight, the centrifugation was carried out at 100,000×g for one hour, and an SDS solubilized product was obtained as a supernatant. To the solubilized product was added the four-folds amount of ethanol under ice-cooling with stirring. The insoluble precipitated *Candida* antigen was collected by centrifugation. The composition of the resulting precipitate was analyzed, and the contents other than water were as follows. Protein 80% by weight, sugar 10% by weight, and nucleic acids 10% by weight, differing from the Ca-LSP antigen solution in that substantially no lipids were contained.

Example 32

Suppression Action of Tumor Metastasis with *Candida* Antigenic Protein

The Ca-LSP antigen solution obtained in Example 1 and IFA were used to prepare a vaccine preparation according to the method described in item 1) of Example 6. The C57BL/6 mice was subcutaneously inoculated with 20 μg protein of the vaccine preparation twice in a one-week interval. For control, a mixture of physiological saline and IFA was inoculated in the same manner as above. One week after the final administration, 0.2 ml of a suspension of B16BL6 melanoma cells at a cell density of $2.5\times10^5$ cells/ml was inoculated to each group of mice via tail vein. A suspension of physiological saline of *Candida* antigen produced in Example 31 at a concentration of 50 μg protein/ml was intravenously inoculated in an amount of 0.2 ml per mouse to a half of each group of mice three times: One day before the melanoma cell inoculation, one day later, and three days later. To the remaining half of each group of mice, a suspension of physiological saline of *Candida* antigen produced in Example 31 at a concentration of 1.25 mg protein/ml was orally administered in an amount of 0.2 ml per mouse for five consecutive days starting from one day before the melanoma inoculation. On the fourteenth day after the melanoma inoculation, the mice were killed, and both lungs were aseptically excised, and the number of formed metastatic nodules was counted. The results thereof are shown in Table 15. It is clear from the table that the metastasis of the tumor is prominently suppressed by intravenously inoculating the *Candida* antigen, and that the metastasis of the tumor can be also suppressed by orally administering the antigen with somewhat less effectiveness than that intravenously inoculated.

Table 15

TABLE 15

| Group Administered with | Method of Administration | Number of Formed Metastatic Nodules ± SD in Lung |
|---|---|---|
| Ca-LSP | Intravenous Administration | 24 ± 17 |

TABLE 15-continued

| Group Administered with | Method of Administration | Number of Formed Metastatic Nodules ± SD in Lung |
|---|---|---|
| Physiological Saline | Intravenous Administration | 150 ± 45 |
| Ca-LSP | Oral Administration | 123 ± 39 |
| Physiological Saline | Oral Administration | 159 ± 39 |

Example 33

Antigenic Cross-Reactivity Between Yeasts of *Kluyveromyces* sp. and *Candida albicans*

Each of *Kluyveromyces* (*K.*) *marxianus* IFO 1735, *K. lactis* IFO 1903 and *C. albicans* TIMM 1768 was cultured in the YPD medium. Each of the resulting living cell suspensions was mixed with IFA in a 1:1 ratio by volume to make up a final cell density of $5 \times 10^7$ cells/ml. Separately, a liquid mixture was prepared by mixing physiological saline with IFA in a 1:1 ratio by volume. 0.1 ml each of the four separate liquid mixtures prepared above was subcutaneously inoculated to C57BL/6 mice twice in a one-week interval. After one week from the final administration of the suspension, 50 µl of the Ca-LSP antigen solution obtained in Example 1, in which the concentration of protein was 200 µg/ml, was subcutaneously administered to the footpads of each group of mice. Twenty-four hours later, footpad swelling was measured. As shown in Table 16, prominent DTH reaction was also observed for mice administered with either *K. marxianus* or *K. lactis*, with slight weaker reaction as compared to the mice immunized with *C. albicans*.

One week after the final administration, the mice in each group were intravenously infected with 0.5 ml of a cell suspension of *Candida albicans* TIMM 0136 to make up a cell density of $2 \times 10^5$ cells/ml. One week after the infection, the mice were killed, and both kidneys were aseptically excised and homogenized with adding 6 ml of physiological saline to yield a homogenate. The resulting homogenate was diluted twice or twenty times with physiological saline, and thereafter, a 100 µl portion of each dilution was spread over Sabouraud dextrose agar plate medium and cultured at 30° C. for two days. The number of the colonies formed were counted. The results were shown in Table 16.

TABLE 16

| Group Administered with | Swelling of Foodpad ± SD ($\times 10^{-2}$ mm) | Ave. Colony Forming Units ± SD ($\log_{10}$) |
|---|---|---|
| *K. marxianus* | 26.0 ± 6.0 | 3.01 ± 0.74 |
| *K. lactis* | 32.6 ± 11.0 | 3.54 ± 1.25 |
| *C. albicans* | 93.4 ± 31.4 | 1.78 ± 0.00 |
| Physiological Saline | 0.3 ± 11.9 | 3.99 ± 0.56 |

It was found that the cell numbers in kidneys significantly decreased in the mice immunized with *K. marxianus*, with slightly less in its degree as compared with the group of mice immunized with Ca-LSP. Therefore, it was clarified from the above results that the mice acquired protective immunity against *C. albicans* infection. Also, it was found that the cell numbers in kidneys decreased in the mice immunized with *K. lactis*.

INDUSTRIAL APPLICABILITY

The fungal antigen of the present invention can be used as biologic products, such as vaccines, compositions used in desensitization therapy for allergoses, the cytokine releasing agents, and diagnostics for diseases, which are highly effective against infectious diseases caused by fungi. In other words, when compared in its vaccine effects, the fungal antigen of the present invention has the same level of effects as that immunized with the living cells, remarkably superior as compared with conventional fungal antigens. Also, even in the aspect of safety, in the fungal antigen of the present invention, the content of the cell wall components is low besides the facts that no living cells are contained and toxicity is low. Therefore, when used as vaccines or preparations for desensitization therapy, adverse reactions caused by cell wall components such as mannan and glucan can be suppressed, so that the immune reactions which are advantageous to individuals can be strengthened. Also, the fungal antigen shows high sensitivity in the examination of the allergoses.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. An isolated nucleic acid encoding a fungal antigen from *Candida albicans*, comprising the amino acid sequence of SEQ ID NO: 6.

2. The nucleic acid according to claim 1, wherein said nucleic acid comprises the nucleotide sequence of SEQ ID NO: 8.

* * * * *